United States Patent
Biggs et al.

(10) Patent No.: US 8,307,711 B2
(45) Date of Patent: Nov. 13, 2012

(54) APPARATUS FOR INSPECTION OF A FLUID AND METHOD

(75) Inventors: Simon Biggs, Leeds (GB); David Harbottle, Chesterfield (GB)

(73) Assignee: University of Leeds, Leeds, West Yorkshire (GB)

( * ) Notice: Subject to any disclaimer, the term of this patent is extended or adjusted under 35 U.S.C. 154(b) by 278 days.

(21) Appl. No.: 12/867,677

(22) PCT Filed: Feb. 23, 2009

(86) PCT No.: PCT/GB2009/050179
§ 371 (c)(1),
(2), (4) Date: Aug. 13, 2010

(87) PCT Pub. No.: WO2009/104025
PCT Pub. Date: Aug. 27, 2009

(65) Prior Publication Data
US 2011/0000285 A1    Jan. 6, 2011

(30) Foreign Application Priority Data
Feb. 22, 2008  (GB) ................................ 0803257.5

(51) Int. Cl.
*G01N 29/02* (2006.01)
*G01N 11/16* (2006.01)
(52) U.S. Cl. ............. 73/579; 73/1.83; 73/54.41; 73/602
(58) Field of Classification Search .................. 73/579, 73/597, 602, 609, 1.83, 54.41, 64.53
See application file for complete search history.

(56) References Cited

U.S. PATENT DOCUMENTS

| | | | | |
|---|---|---|---|---|
| 3,802,271 | A * | 4/1974 | Bertelson | 73/865.5 |
| 4,312,238 | A * | 1/1982 | Rey | 73/861.28 |
| 5,046,500 | A * | 9/1991 | Fehr | 600/455 |
| 5,148,229 | A * | 9/1992 | Wiseall | 356/28 |
| 7,437,912 | B2 * | 10/2008 | Sparks et al. | 73/54.01 |
| 2004/0255648 | A1 | 12/2004 | Sparks | |
| 2006/0031030 | A1 | 2/2006 | Bennett et al. | |
| 2006/0107733 | A1 | 5/2006 | Aastrup et al. | |

FOREIGN PATENT DOCUMENTS

| | | |
|---|---|---|
| DE | 19601695 A1 | 7/1997 |
| DE | 19725012 C1 | 11/1998 |
| DE | 19850803 A1 | 5/2000 |
| DK | WO0066266 A1 | 11/2000 |
| WO | WO0212873 A1 | 2/2002 |

OTHER PUBLICATIONS

K. Keiji Kanazawa et al., "The Oscillation Frequency of a Quartz Resonator in Contact with a Liquid", Analytica Chimica Acta, 175 (1985) pp. 99-105.
Eggers, F. et al., "New piano-concave ultrasonic resonator cells for absorption and velocity measurements in liquids below 1 Mhz", Measurement Science & Technology, vol. 5, No. 9, Bristol, GB, pp. 1131-1138 (Sep. 1994).

* cited by examiner

*Primary Examiner* — J M Saint Surin
(74) *Attorney, Agent, or Firm* — Ward and Smith, P.A.

(57) ABSTRACT

Apparatus for inspection of a fluid comprising: a channel portion, the channel portion having a channel inlet and a channel outlet separate from the channel inlet; a piezoelectric sensor element provided at a sensor position of the channel and arranged to contact fluid flowing through the channel portion from said channel inlet to said channel outlet, the apparatus being configured to determine a difference value being a value corresponding to a difference between a resonant frequency of oscillation of said piezoelectric element at a given moment in time and a reference resonant frequency.

24 Claims, 36 Drawing Sheets

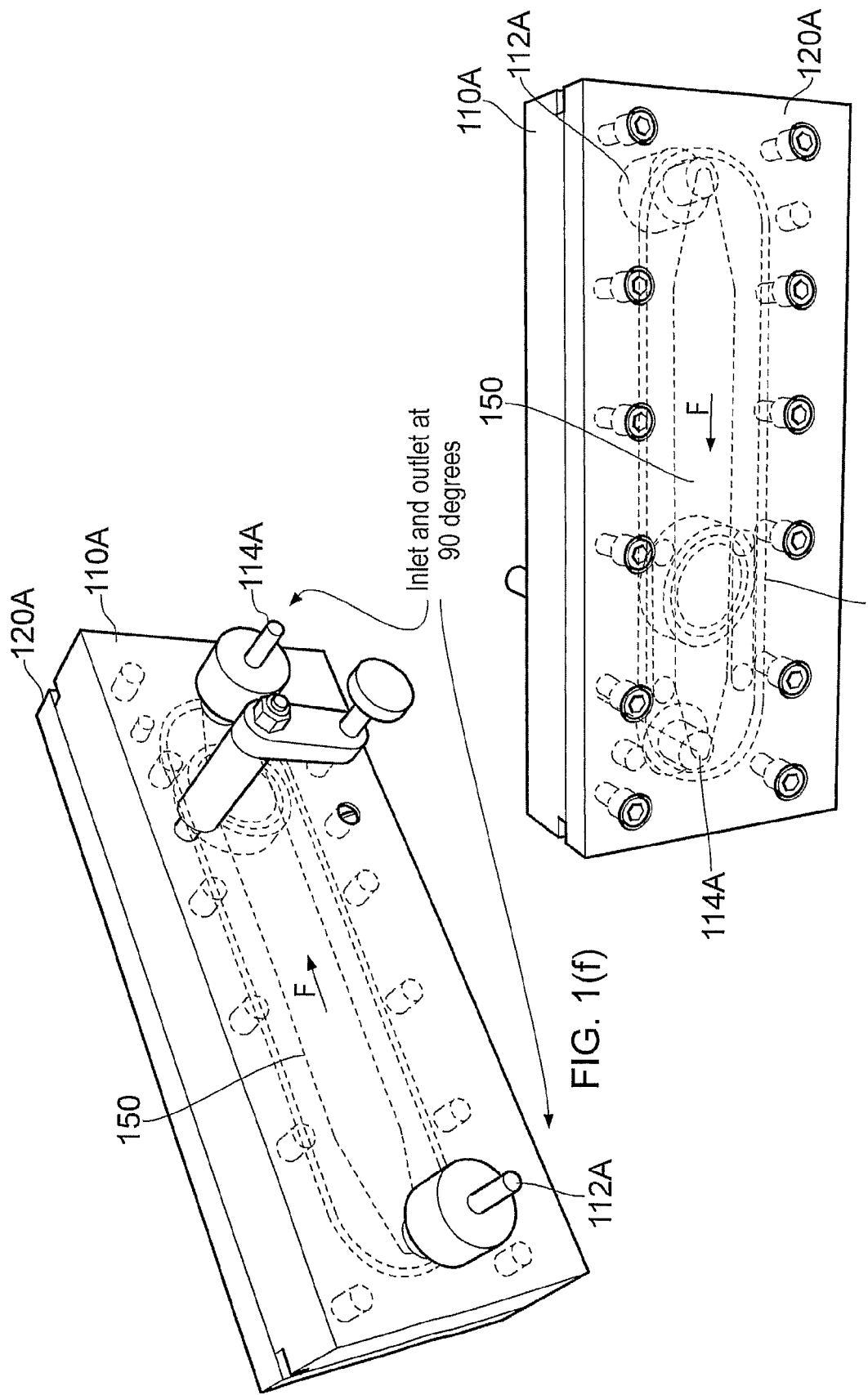

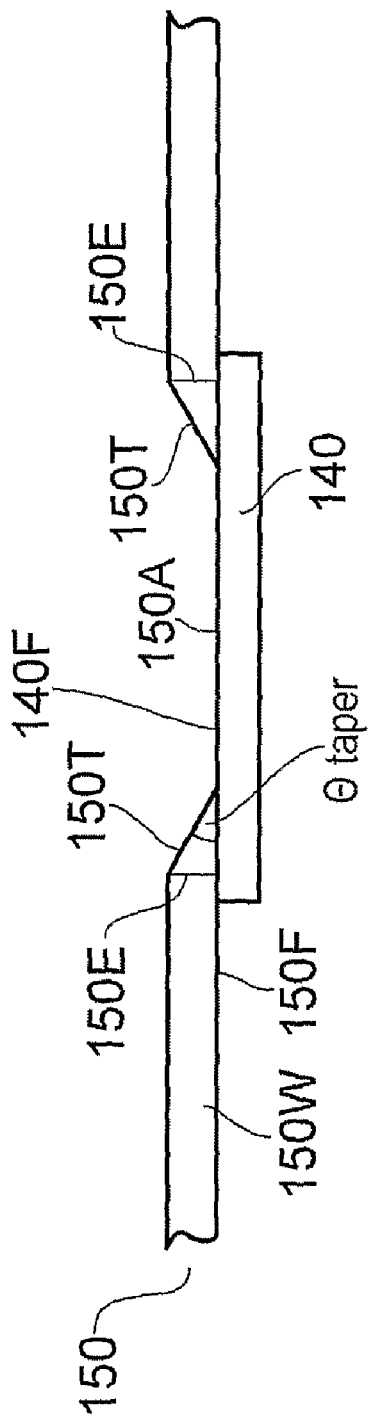
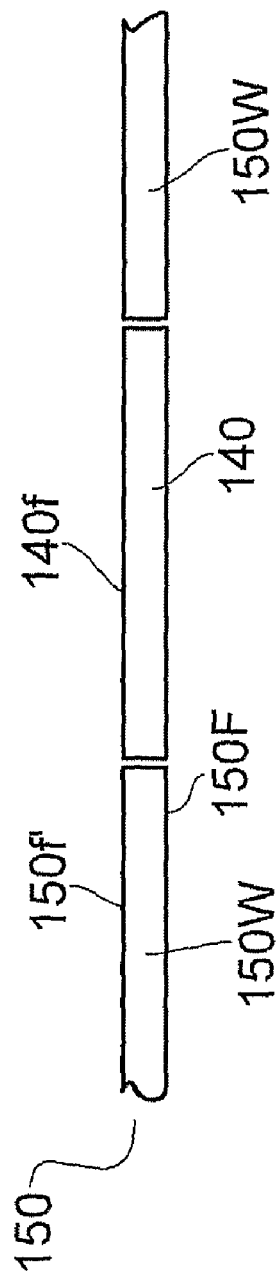

| Compound | Yield stress range | Yield stress (Pa) |
|---|---|---|
| Titania: | | |
| | (10Pa—60Pa) | $(\Delta F + 1774)/17.2$ |
| | (60Pa — 120Pa) | $(\Delta F + 784)/0.34$ |
| Kaolin: | | |
| | (10Pa— 120Pa) | $(\Delta F + 1120)/6.15$ |
| Bentonite: | | |
| | (0Pa — 500Pa) | $(\Delta F + 897)/2.48$ |
| Talcum Powder: | | |
| | (50Pa — 200Pa) | $(\Delta F + 698)/2.74$ |

FIG. 4

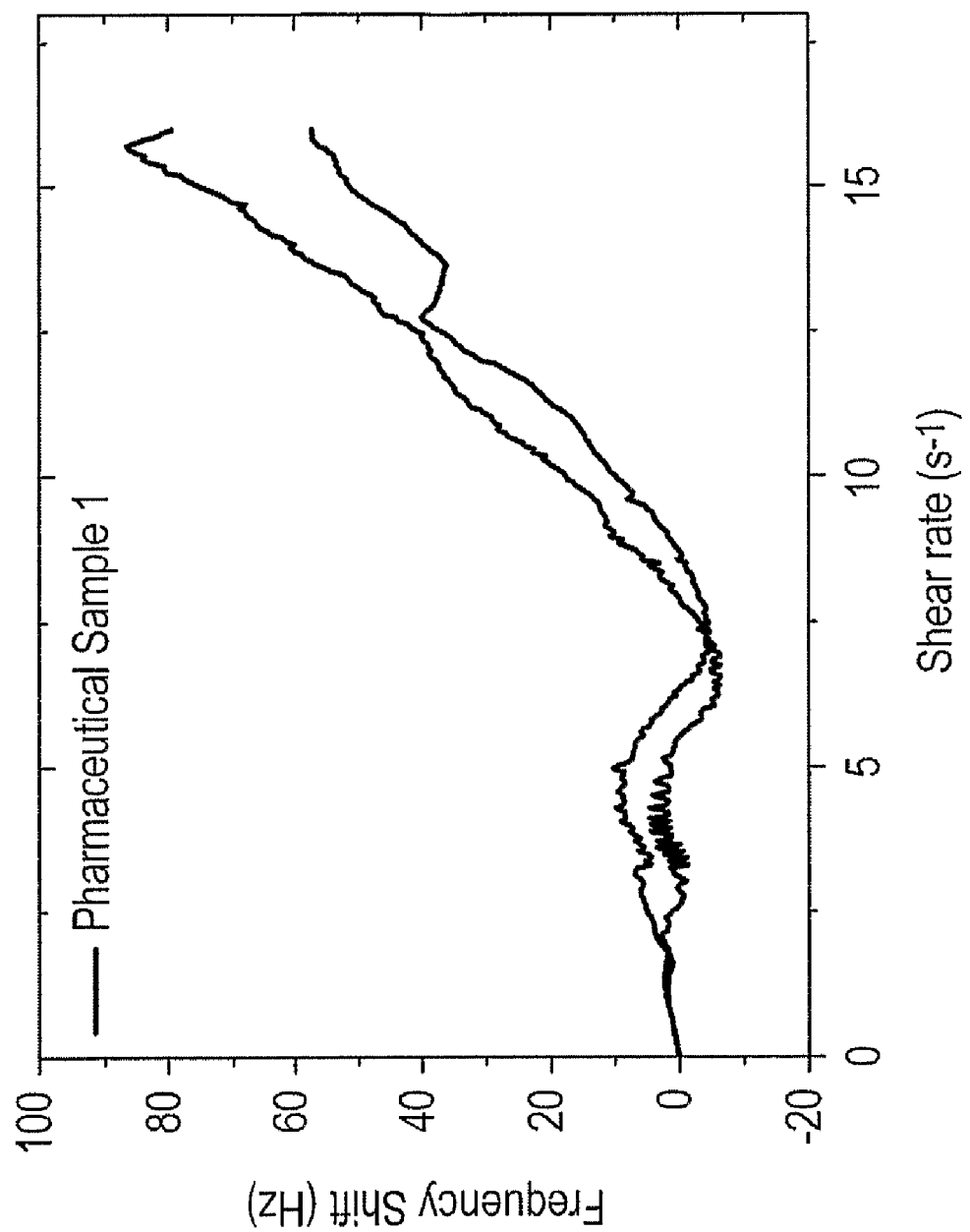

APPARATUS FOR INSPECTION OF A FLUID AND METHOD

FIELD OF THE INVENTION

The present invention relates to apparatus for inspection of a fluid and to a method of inspection of a fluid. By the term 'fluid' is included reference to complex fluids and particulate fluids in addition to simple fluids. By the term fluid is therefore included reference to slurries and to pastes, as well as to fluids in the form of particles of a substantially dry powder.

BACKGROUND

It is known to measure the viscosity of a fluid using a variety of types of apparatus. U.S. Pat. No. 5,565,620 discloses a method for measuring rheological properties of a fluid and a rheometer for carrying out the method. The document discloses measuring rheological properties of a sample by causing an oscillation system containing the sample to perform free oscillations. Damping caused by the sample is detected and hence viscosity can be measured. The apparatus is disclosed to be especially adapted to measure body fluids.

WO9749980 discloses an electronic viscometer having a vibrating drive in a hollow probe. The vibrating drive is configured to cause the hollow probe to oscillate in an axial direction; a feedback electrode tracks the resonant frequency of the drive. The viscometer measures viscosity of a fluid by monitoring changes in the resonant frequency of the viscometer.

BRIEF SUMMARY OF THE DISCLOSURE

In a first aspect of the invention there is provided apparatus for inspection of a fluid comprising: a channel portion, the channel portion having a channel inlet and a channel outlet separate from the channel inlet; a piezoelectric sensor element provided at a sensor position of the channel and arranged to contact fluid flowing through the channel portion from said channel inlet to said channel outlet, the apparatus being configured to determine a difference value $\Delta F_r$ being a value corresponding to a difference between a resonant frequency of oscillation of said piezoelectric element at a given moment in time and a reference resonant frequency.

By channel is meant a passageway through which a fluid may be passed. In some embodiments the channel has an open channel portion. In some embodiments fluid in the passageway is exposed to an ambient environment at the portion of the channel that is open.

In some embodiments the passageway is closed, fluid in the channel not being exposed to an ambient environment. This configuration is generally preferred.

Preferably in this and other aspects of the invention the reference resonant frequency corresponds to a resonant frequency of the crystal upon exposure to a predetermined medium such as a fluid under predetermined conditions. In some embodiments the predetermined conditions are room temperature and standard atmospheric pressure. In some embodiments the conditions correspond to conditions of standard temperature and pressure (STP). In some embodiments the medium is air, whilst in some embodiments the medium is water. Other conditions are also useful. Other media to which the crystal is exposed to perform the measurements are also useful.

Apparatus according to some embodiments of the invention has the advantage that handling of the fluid under inspection is made easier.

Preferably the piezoelectric sensor element is provided at a wall of the channel.

Preferably a plane of a face of the sensor element exposed to fluid flowing through said channel is oriented generally parallel to a direction of flow of fluid through said channel.

More preferably the channel is shaped to promote fully developed laminar flow of fluid through the channel at the sensor position.

Preferably the channel has a build-up portion, the build-up portion comprising a length of the channel spanning a distance from the piezoelectric element in a direction towards the inlet, the build-up portion being of generally constant cross-sectional area.

Preferably the build-up portion of the channel is arranged whereby a flow direction of fluid flowing through the build-up portion is substantially straight.

Preferably the build-up portion is substantially straight-walled along said flow direction.

Preferably the wall of the channel is provided with a sensor aperture therein, a face of the element exposed to the channel being provided within said sensor aperture. Preferably the face of the element is substantially flush with an inner face of the wall of the channel.

Alternatively the face of the element may be recessed with respect to an inner surface of the wall of the channel.

Preferably a portion of the wall around at least a portion of the sensor aperture is shaped to promote the smooth flow over the element of fluid at or close to the wall upstream of the element.

More preferably the portion of the wall around at least a portion of the sensor aperture is tapered towards the element.

The channel inlet may have a cross-sectional area lower than a cross-sectional area of a portion of the channel at the sensor position, a portion of opposed regions of a wall of the channel in contact with fluid and located between the channel inlet and the element being arranged whereby an angle of divergence of said regions with respect to one another is configured to promote obtaining the fully developed laminar flow of fluid.

Preferably the angle of divergence is in the range from about 5° to about 180°.

More preferably the angle of divergence is in the range from about 40° to about 180°, optionally from about 40° to about 120°.

Still more preferably the angle of divergence is about 90°.

The channel portion may be shaped and configured whereby a fluid flowing through the channel portion experiences squeeze flow whereby the channel is substantially entirely filled with fluid.

Preferably the channel outlet is of a lower cross-sectional area than that of the channel at the sensor position, the channel being shaped whereby a portion of opposed regions of a wall of the channel in contact with fluid and located between the channel outlet and the element is arranged whereby an angle of convergence of said regions with respect to one another is sufficiently high to promote establishment of a back pressure on fluid flowing through the channel thereby to cause the channel to be filled with fluid.

The angle of convergence may be in the range from about 5° to about 180°.

Preferably the angle of convergence of the channel is in the range from about 40° to about 90°.

More preferably the angle of convergence is in the range from about 40° to about 90°.

Still more preferably the angle of convergence is about 90°.

The apparatus may be provided with a swirl pipe generally upstream of the channel, the swirl pipe being configured to develop swirl in a fluid flowing into the channel.

Preferably the swirl pipe comprises a pipe having a plurality of helical channels formed in an interior sidewall of the pipe along at least a portion of a length of the pipe.

More preferably the pipe comprises four helical channels formed in the interior sidewall.

The channel outlet may be provided with a bend portion whereby the direction of fluid flow from said channel is changed.

Preferably the bend portion is arranged to change the direction of fluid flow by an angle of at least 20°.

The bend portion may be arranged to direct the fluid in a generally upwards direction. The channel portion may be arranged whereby fluid flows through the channel in a substantially horizontal plane.

The apparatus may comprise a plurality of piezoelectric elements at mutually spaced apart locations along a length of the channel, the elements being arrange to contact fluid flowing through the channel.

Preferably a portion of the channel proximate the channel inlet has a first cross-sectional area and a portion of the channel proximate the channel outlet has a second cross-sectional area, the first cross-sectional area being greater than the second cross-sectional area.

The cross sectional area of the channel may be arranged to decrease over a portion of the channel between each adjacent pair of elements whereby the cross-sectional area decreases progressively from said portion of the channel having the first cross-sectional area to the portion of the channel having the second cross-sectional area.

Preferably the apparatus is operable to allow a fluid to be passed through the channel at a constant flow rate, the apparatus being configured to measure a difference value $\Delta F_r$ of each element as fluid is passed through the channel.

The apparatus may be configured to determine a viscosity of said fluid at a location of each of said plurality of elements based on values of $\Delta F_r$ determined by each of said plurality of elements.

Preferably the apparatus is arranged to determine the value of the viscosity of the fluid from said values of $\Delta F_r$ by means of at least one selected from amongst reference to a look-up table and an algorithm.

More preferably the inlet has an inlet aperture having a first diameter and the outlet has an outlet aperture of a second diameter wherein the first and second diameters are in the range from around 1 μm to around 100 mm.

Still more preferably the first and second diameters are in the range from around 1 μm to around 10 mm, preferably around 1 μm to around 5 mm, more preferably around 1 μm to around 1 mm.

It is to be understood that reference to diameter does not limit the inlet and outlet apertures to a circular form. Other shapes of aperture are also useful such as elliptical, oval, quadrilateral such as square or rectangular or any other suitable shape.

The reference resonant frequency may correspond to that of a further piezoelectric crystal arranged to be isolated from the fluid flowing through the channel portion whereby the fluid does not contact the further piezoelectric crystal.

The reference resonant frequency may correspond to that of a further piezoelectric crystal arranged to be isolated from the fluid flowing through the channel portion whereby the fluid does not contact the further piezoelectric crystal.

This feature has the advantage that a direct comparison may be made in real time between the resonant frequency of the crystal in contact with liquid and the resonant frequency of the further piezoelectric crystal, which may be considered to be a reference piezoelectric crystal. In some embodiments this allows automatic compensation to be made for the effects of temperature and/or atmospheric pressure since the reference crystal may be arranged to experience the same temperature and/or atmospheric pressure as the crystal in contact with fluid.

A reference piezoelectric crystal may be used with any of the embodiments described herein.

Preferably the fluid comprises a liquid.

Preferably the fluid comprises particles of a material.

The fluid may comprise at least one selected from amongst a suspension, a slurry and a paste.

In a second aspect of the invention there is provided apparatus as claimed in any preceding claim further arranged to measure an amount of surface charge of particles comprised in the fluid, the apparatus being configured to cause the piezoelectric element to oscillate at a resonant frequency of the element at a first amplitude of oscillation, the apparatus being further arrange to increase an amplitude of oscillation of the element above the first amplitude until a final amplitude of oscillation is attained whereat a rate of change of resonant frequency with amplitude of oscillation is below a prescribed rate, the apparatus being further configured to provide an output corresponding to an amount of surface charge of particles of the fluid based on a difference between the final resonant frequency data value and a reference resonant frequency value, the reference resonant frequency value corresponding to a reference resonant frequency, the reference resonant frequency being the resonant frequency of the element under predetermined conditions.

Preferably the predetermined conditions correspond to exposure of the element to a prescribed fluid, optionally with a prescribed amplitude of oscillation, further optionally the fluid being the fluid under inspection, still further optionally the conditions corresponding to room temperature and standard pressure. The prescribed amplitude of oscillation may be a value of amplitude that is around 10% to around 20%, preferably around 15% of the final amplitude of oscillation.

The apparatus may be configured to provide said output in the form of a value of a zeta potential of the fluid.

Preferably the apparatus is configured to provide said output by means of at least one selected from amongst reference to a look-up table and an algorithm.

In a further aspect of the invention there is provided apparatus for measuring an amount of surface charge of particles comprised in a fluid, comprising: a piezoelectric element arranged to contact a fluid to be measured, the apparatus being configured to cause said element to oscillate at a resonant frequency of the element, the apparatus being further arranged to increase an amplitude of oscillation of the element until a final amplitude of oscillation is attained whereat a change in resonant frequency of the element for a given increase in amplitude of oscillation is less than a prescribed value, and to determine a data value corresponding to a final resonant frequency of the element being the resonant frequency when the element is in contact with the fluid and the element is oscillating at the final amplitude value, the apparatus being further configured to provide an output corresponding to an amount of surface charge of particles of the fluid based on a difference between the final resonant frequency data value and a reference value, the reference value corresponding to a reference resonant frequency, the reference resonant frequency being the resonant frequency of the element under predetermined conditions.

In a third aspect of the invention there is provided a dip probe device for inspection of a fluid comprising: a body portion; and a piezoelectric element coupled to the body portion, the device being operable to expose the piezoelectric element to a fluid in which the device is dipped, the device being further operable to excite said element thereby to induce oscillation of the element at a resonant frequency of the element, the apparatus being configured to determine a difference value corresponding to a value of a difference between the resonant frequency of said piezoelectric element at a given moment in time and a reference frequency being the resonant frequency of the element under predetermined conditions.

Preferably the body portion is provided with a free end having a tapered form.

A thickness of the body portion is preferably lower along a direction perpendicular to a plane of the piezoelectric element compared with that along a direction parallel to the plane of the piezoelectric element.

The device may comprise a plurality of piezoelectric elements.

Preferably the device is operable selectively to expose respective different piezoelectric elements to said fluid.

The piezoelectric elements may be provided in a carousel.

The device may be provided with a cover plate rotatable with respect to the body portion whereby a selected one or more piezoelectric elements may be exposed to the fluid.

Alternatively the carousel may be rotatable with respect to the body portion whereby a selected one or more piezoelectric elements may be exposed to the fluid.

More preferably the device is operable to provide an output of a value corresponding to at least one selected from amongst a value of a yield stress, solids concentration and viscosity of the fluid.

Preferably the device is configured to provide said value by means of at least one selected from amongst a look-up table and an algorithm.

The device may be configured to be dipped in the fluid manually.

Preferably the predetermined conditions correspond to a predetermined temperature and pressure.

The predetermined temperature and pressure may correspond to room temperature and standard pressure.

In a fourth aspect of the invention there is provided a method of inspecting a fluid comprising the steps of: passing a fluid through a channel having a channel inlet and channel outlet, the channel being provided with a piezoelectric sensor element at a sensor position of the channel, the element being arranged to contact fluid flowing through the channel portion from said channel inlet to said channel outlet; determining a difference value $\Delta F_r$ being a value corresponding to a difference between a resonant frequency of oscillation of said piezoelectric element at a given moment in time and a reference resonant frequency.

Preferably the method further comprises the step of providing an output corresponding to the value of the yield stress of the fluid based in the difference value $\Delta F_r$.

Some embodiments of the invention have the advantage that a measurement of yield stress may be made in a rapid and convenient manner. Some embodiments of the invention are suitable for integration into a production facility.

Some embodiments of the invention are suitable for use in portable rheometers.

Preferably the method comprises comparing said data value with a reference data value corresponding to a reference resonant frequency being the resonant frequency of the element under predetermined conditions thereby to obtain a resonant frequency difference value $\Delta F_r$ characteristic of the yield stress of the fluid.

Preferably the data value is obtained with the fluid in a substantially static, no-flow condition.

This has the advantage of increasing an accuracy with which yield stress of a fluid may be measured.

The output corresponding to the value of the yield stress of the fluid may be provided by reference to at least one selected from amongst a look-up table and an algorithm, the algorithm defining a relationship between $\Delta F_r$ and yield stress of the fluid.

The method may further comprise the step of performing a calibration operation.

The step of performing the calibration operation may comprises the steps of: measuring a calibration difference value corresponding to the difference between the reference resonant frequency of the element and the resonant frequency of the element in a reference fluid having a known value of yield stress; and storing a calibration value being a value corresponding to said calibration difference value.

The method may comprise the step of providing an alert in the event that said difference value $\Delta F_r$ exceeds a first predetermined critical value.

The method may comprise the step of providing an alert in the event that said difference value $\Delta F_r$ is less than a second predetermined critical value.

The piezoelectric element may be dipped into a fluid by a user.

The piezoelectric element may be provided in a portion of a portable housing configured to be carried by a user, the housing being configured to be dipped in a fluid thereby to place the element in contact with the fluid.

The housing may comprise a plurality of elements, the housing being operable to expose a selected one of said plurality of elements to fluid according to a user's requirement.

This has the advantage that if a crystal is or becomes damaged, contaminated or otherwise unusable the user can select a fresh crystal for performing measurements. A crystal may become damaged due for example to chemical attack or mechanical damage.

The housing may be arranged to prevent contact between the fluid and one or more of said plurality of elements when the housing is dipped in the fluid.

The element may be provided in a channel of a housing at a sensor position of the channel, the housing having a channel inlet and a channel outlet, the housing being configured to direct fluid flowing through the housing between the channel inlet and the channel outlet to flow over and in contact with said element.

Preferably the housing is shaped and configured to promote fully developed laminar flow of fluid over the element under dynamic flow conditions.

The channel may be arranged whereby a portion of opposed regions of a wall of the channel in contact with fluid and located between the channel inlet and the element is arranged whereby an angle of divergence of said regions with respect to one another is in the range from about 5° to about 180°.

The angle of divergence may be in the range from about 40° to about 180°.

Still more preferably the angle of divergence is about 90°.

Preferably a portion of the channel located from the piezoelectric element in a direction towards the inlet may be of generally constant cross-sectional area.

Preferably the housing is shaped and configured whereby a fluid flowing through the housing experiences squeeze flow whereby the channel is substantially entirely filled with fluid.

Preferably the channel outlet is of a lower cross-sectional area than that of the channel at the sensor position.

Preferably the channel is arranged whereby a portion of opposed regions of a wall of the channel in contact with fluid and located between the channel outlet and the element is arranged whereby an angle of convergence of said regions with respect to one another is in the range from about 5° to about 120° thereby to induce squeeze flow.

Preferably the angle of convergence is in the range from about 20° to about 90°.

More preferably the angle of convergence is about 40°.

Preferably the method comprises the step of developing swirl in a fluid flowing into the channel.

Swirl may be developed by providing a swirl device generally upstream of the channel.

The swirl device may comprise a pipe having a plurality of helical channels formed in an interior sidewall of the pipe along at least a portion of a length of the pipe.

Preferably the pipe comprises four helical channels formed in the interior sidewall.

Preferably the channel outlet is provided with a bend portion whereby the direction of fluid flow from said channel is changed.

The bend portion may be arranged to change the direction of fluid flow by an angle of at least 20°, preferably around 90°.

Preferably the bend portion is arranged to direct the fluid in a generally upwards direction.

The housing may comprise a plurality of piezoelectric elements at mutually spaced apart locations along a length of the channel, the elements being arrange to contact fluid flowing through the channel.

Preferably a portion of the channel proximate the channel inlet has a first cross-sectional area and a portion of the channel proximate the channel outlet has a second cross-sectional area, the first cross-sectional area being greater than the second cross-sectional area.

Preferably the cross sectional area of the channel is arranged to decrease over a portion of the channel between each adjacent pair of elements whereby the cross-sectional area decreases progressively from said first cross-sectional area at the channel inlet to the second cross-sectional area at the channel outlet.

Preferably the method comprises the step of allowing a fluid to be passed through the channel at a constant flow rate, and measuring a difference value $\Delta F_r$ of each element as the fluid is passed through the channel.

Preferably the method further comprises determining a viscosity of said fluid at a location of each of said plurality of elements based on values of $\Delta F_r$ determined by each of said plurality of elements.

Preferably the method comprises determining the value of the viscosity of the fluid from said values of $\Delta F_r$.

The method may comprise determining the value of the viscosity by means of at least one selected from amongst reference to a look-up table and an algorithm.

Alternatively or in addition the method may comprise the step of determining a solids concentration of the fluid based on the resonant frequency difference value $\Delta F_r$.

In a fifth aspect of the invention there is provided a method of measuring an amount of surface charge of particles of a fluid comprising the steps of: (a) placing a piezoelectric element in contact with a fluid to be measured; (b) causing the element to oscillate at a resonant frequency of the element; (c) increasing the amplitude of oscillation of the element until a rate of change of resonant frequency with amplitude is less than a predetermined threshold value, the value of the amplitude of oscillation at this stage being a final amplitude value; (d) obtaining a data value corresponding to a final resonant frequency of the element being the resonant frequency when the element is in contact with the fluid and the element is oscillating at the final amplitude value; (e) providing an output corresponding to an amount of surface charge of particles of the fluid based on a difference between the data value and a reference value corresponding to a reference resonant frequency, the reference resonant frequency being the resonant frequency of the element under predetermined conditions.

This feature has the advantage that a measurement of surface charge can be obtained in a rapid and convenient manner. The method requires no consumable materials (with the exception in some embodiments of the piezoelectric element which is disposable in some embodiments).

Preferably the predetermined conditions correspond to exposure of the element to a prescribed fluid, optionally with a prescribed amplitude of oscillation, further optionally the fluid being the fluid under inspection, still further optionally the conditions corresponding to room temperature and standard pressure.

Preferably the apparatus is configured to provide said output in the form of a value of a zeta potential of the fluid.

Preferably the apparatus is configured to provide said output by means of at least one selected from amongst a look-up table and an algorithm.

In a further aspect of the invention there is provided a method of measuring an amount of surface charge of particles comprised in a fluid, comprising the steps of: (a) placing a piezoelectric element in contact with a fluid to be measured; (b) exciting the piezoelectric element electrically to induce oscillation at a resonant frequency of the element at a first amplitude of oscillation and increasing the amplitude of oscillation of the element above the first amplitude until a final amplitude of oscillation is attained whereat a rate of change of resonant frequency with increasing amplitude of oscillation is below a prescribed rate; (c) obtaining a data value corresponding to a final resonant frequency of the element being the resonant frequency when the element is in contact with the fluid and the element is oscillating at the final amplitude value; (d) providing an output corresponding to an amount of surface charge of particles of the fluid based on a difference between the data value and a reference value, the reference value corresponding to a reference resonant frequency, the reference resonant frequency being the resonant frequency of the element under predetermined conditions.

BRIEF DESCRIPTION OF THE DRAWINGS

Embodiments of the invention will now be described with reference to the accompanying figures in which:

FIG. 4 is a table showing empirical formulae for calculating yield stress as a function of $\Delta F_r$ for some common compounds used to form particulate fluids;

DETAILED DESCRIPTION

In one embodiment of the invention, apparatus is provided in the form of a housing or body portion connectable to a source of a fluid to be analysed. It is to be understood that the apparatus is connectable to a source of a variety of fluids including simple fluids, complex fluids and particulate fluids.

Figure 1:
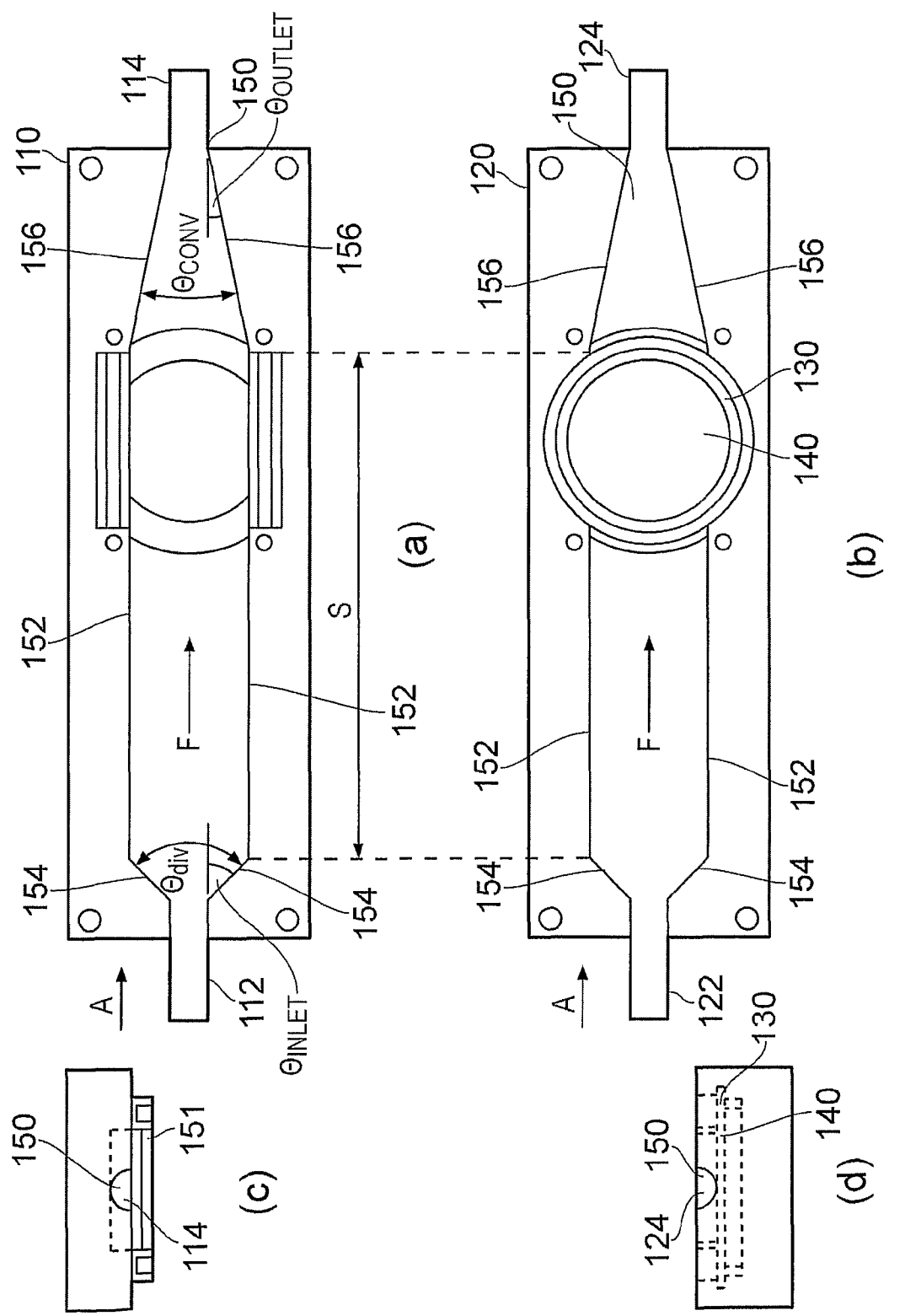
FIGS. 1 (a) to (k) show inspection apparatus according to embodiments of the invention.

In the embodiments of FIG. 1 the apparatus is provided in the form a pair of sections joined together to form a channel, the sections being a cover section 110 (FIG. 1(a)) and a base section 120 (FIG. 1(b)). When connected to one another, the two sections together define a fluid-tight passageway or channel 150 through which a fluid may be passed, the channel 150 having an inlet 112, 122 and an outlet 114, 124.

The base section 120 is provided with a recessed portion 130 in which a piezoelectric crystal 140 may be provided. The piezoelectric crystal 140 is exposed to the channel 150 on one side of the crystal. In some embodiments a seal member 151 is provided in abutment with the crystal 140, the seal member being arranged to prevent leakage of fluid out from the channel region. In some embodiments a seal member is provided on each side of the crystal, with pressure being applied to the crystal to aid compression of the seal members to form a fluid-tight seal.

In the embodiment of FIG. 1 the channel is shaped to promote fully developed flow conditions at the surface of the crystal when fluid flows in the direction of arrow 'F' of FIG. 1. To this end, it can be seen in FIG. 1(a) and (b) that a portion "S" of a length of the channel 150 which includes a portion of the channel at which the crystal is located is provided with generally parallel walls 152 in order to promote such flow conditions. A portion of the channel between the section S and the channel inlet 112, 122 has a section having opposed walls having 154 an angle of divergence ($\theta_{div}$) with respect to one another of around 90°. This angle is twice the value of an angle $\theta_{inlet}$ (around)45° shown in FIG. 1(a).

The presence of an angle of divergence of walls 154 less than 180° promotes the maintaining of contact between a fluid entering the channel 150 through the inlet 112, 122 and walls of the channel in order to reduce a risk of the introduction of bubbles or other voids into the fluid.

In some embodiments of the invention inlet angle $\theta_{inlet}$ is in the range from around 5° to around 180°, preferably from around 10° to around 90°. In some embodiments $\theta_{inlet}$ is in the range from around 10° to around 20°.

In some embodiments the channel is also shaped to promote filling of the channel with fluid so that an entire surface of the crystal 140 exposed to the channel is coated with fluid. This feature reduces a risk of misleading data being generated by the apparatus.

For example, in some situations the change in resonant frequency $\Delta F_r$ of the crystal 140 is at least partly determined by an extent to which the crystal is coated with fluid. If portions of the crystal surface exposed to the channel are not coated with fluid the change in resonant frequency of the crystal may be different from the value in the case that the exposed surface is entirely coated with fluid.

Thus, in some embodiments of the invention, including the embodiment of FIG. 1, the housing is shaped to promote 'squeeze flow' of fluid through the channel. In other words, the channel is shaped such that a back pressure is exerted on fluid contained in the channel by fluid at or approaching the channel outlet.

To this end, as can be seen in FIGS. 1 (a) and (b) a portion of the channel 150 between section S and the outlet 114, 124 is provided with opposed walls 154 having an angle of convergence ($\theta_{conv}$) with respect to one another of around 40°.

By angle of convergence or angle of divergence is meant an angle between the planes of the portions of the opposed walls in a plane containing a direction of flow of fluid through the channel 150.

In some embodiments the outlet angle $\theta_{outlet}$ (FIG. 1(a)) being half the angle of convergence $\theta_{conv}$ is in the range from around 20° to around 90°, preferably around 20° to around 60°, more preferably around 30°. In the embodiment shown in FIG. 1 the outlet angle $\theta_{outlet}$ is around 20°. In some embodiments the outlet angle is from around 20° to around 40°.

Figure 1E:
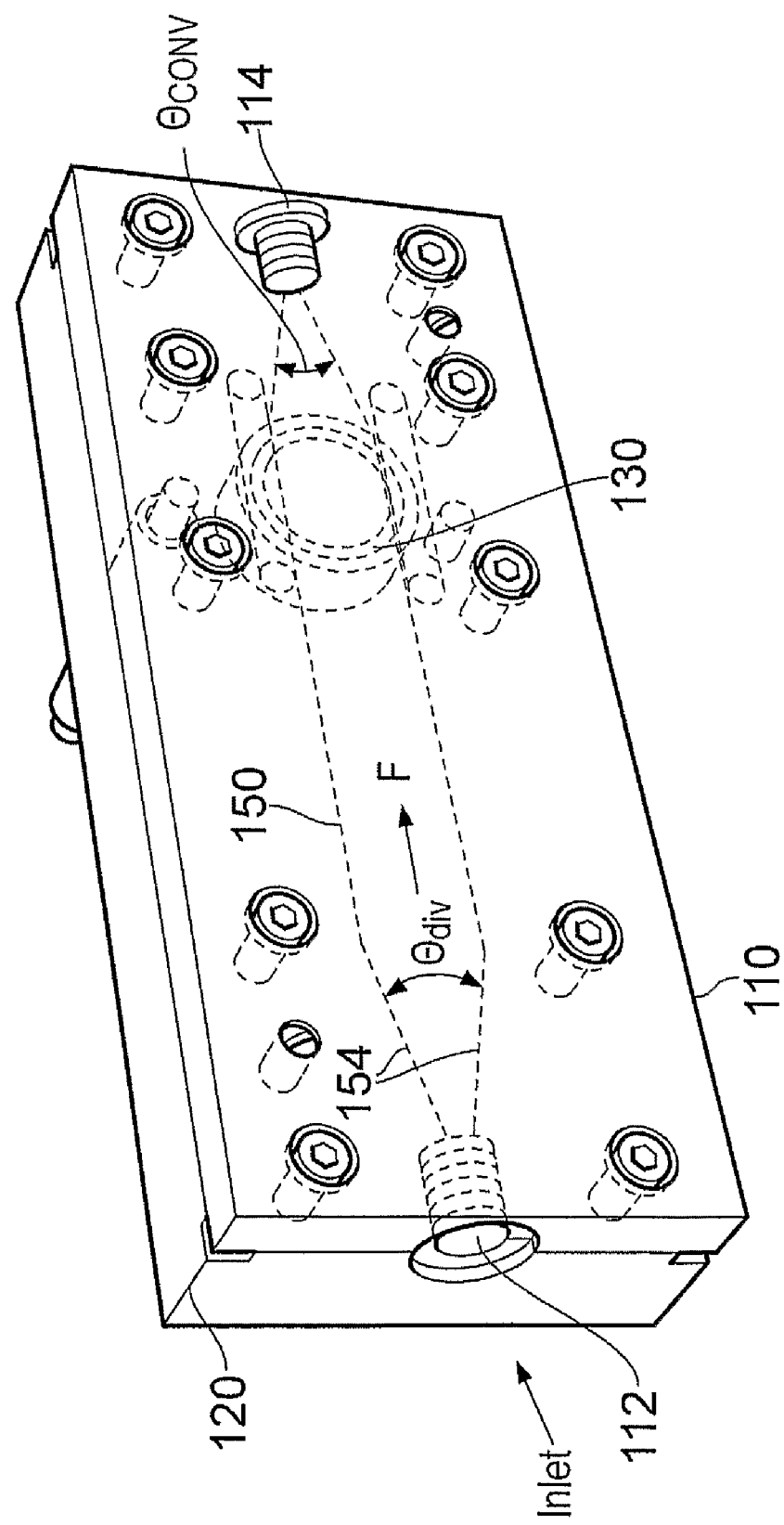

FIG. 1(e) shows an embodiment in which the inlet angle $\theta_{inlet}$ is around 20° and the outlet angle $\theta_{outlet}$ is around 45°. It can be seen that a screw thread has been formed in the apparatus at each of the inlet and outlet apertures, which are arranged in a 'straight through' configuration. In other words, the inlet 112, 122 and outlet 114, 124 are arranged such that fluid flowing into the channel enters the inlet aperture flowing along a direction generally parallel to the flow direction F, and fluid flowing out from the channel passes through the fluid outlet aperture flowing along a similar direction.

FIG. 1(f), (g) show an embodiment of the invention in which the inlet and outlet apertures are arranged such that fluid flowing into the channel passes through the inlet aperture flowing along a direction generally normal to the flow direction F. Fluid flowing out from the channel passes through the fluid outlet aperture along a direction normal to the flow direction F and in a direction opposite that of fluid flowing through the channel inlet aperture.

The embodiment of FIG. 1(f), (g) has the feature that in the case that the channel outlet 114A is oriented in a generally vertical orientation, a pressure of fluid in the channel will be increased due to gravity. This results in an increase in 'squeeze flow' through the channel thereby promoting filling of the channel with fluid.

A further advantage of the embodiment of FIG. 1(f), (g) is that the channel inlet 112A and outlet 114A apertures are not formed from two separate portions 110A 120A of the apparatus. Rather, the apertures are unitary apertures formed in portion 110A. In some embodiments this feature has the advantage that a risk of leakage of fluid from the apparatus in service is thereby reduced.

In some embodiments of the invention, a depth of the channel being a dimension of the channel along a direction normal to the plane of fluid flow is from around 0.5 mm to around 5 mm. In some embodiments the length 'S' (FIG. 1) is from around 30 mm to around 120 mm for a channel depth of around 0.5 mm and from around 140 mm to around 220 mm for a channel depth of around 5 mm. In some embodiments a width of the channel is around 10-20 mm.

In some embodiments a diameter of the inlet and outlet apertures is substantially the same as a depth of the channel.

FIGS. 1(h) and 1(i) show expanded views of the manner in which the crystal 140 is attached to a wall 150W of the channel in some embodiments of the invention.

In the embodiment of FIG. 1(h) the crystal 140 is placed in abutment with an external face 150F of the wall of the channel 150W around an aperture 150A formed in the wall 150W.

In this embodiment an edge 150E of the wall 150W defining the aperture 150A is generally perpendicular to a face 140F of the crystal exposed to fluid in the channel 150. This feature can result in the presence of gas bubbles or other inhomogeneities in the composition of fluid at the surface 140F of the crystal 140.

Thus, in some embodiments of the invention, instead of forming an abrupt edge 150E, a tapered edge 150T is formed. This has the advantage that a likelihood of introducing bubbles and other inhomogeneities in the fluid is reduced.

In FIG. 1(h) a dashed line 150T corresponds to the shape of a tapered edge according to some embodiments of the invention having an angle of taper $\theta_{taper}$ of around 20°. Other angles of taper are also useful. In some embodiments a curved or at least partially curved edge is provided instead of or in addition to a tapered edge.

It will be appreciated that in some embodiments a seal member is provided between the face 140F of the crystal 140 and the wall 150W.

In some embodiments, the crystal is positioned such that a face 140F of the crystal 140 is generally flush with an inner face 150F' of the wall 150W of the channel 150. In some embodiments a seal member is provided around an outer peripheral edge of the crystal 140 whereby a seal is formed in a generally radial direction between the crystal 140 and the wall 150W of the channel 150.

Figure 1J:
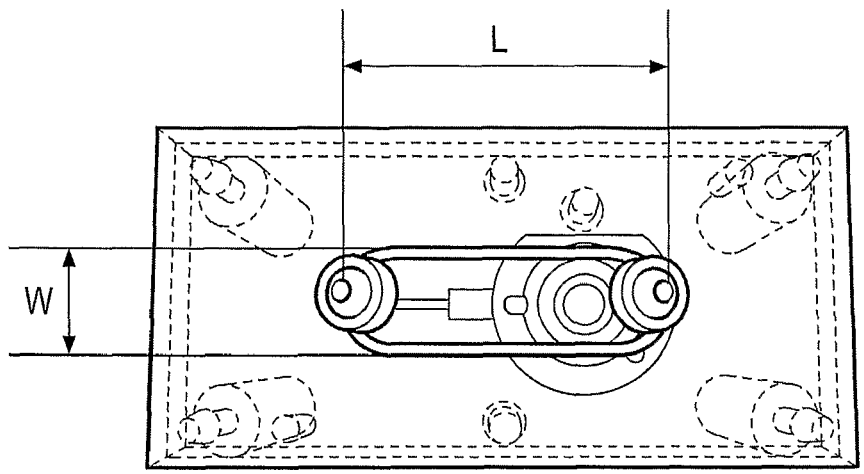
Figure 1K:
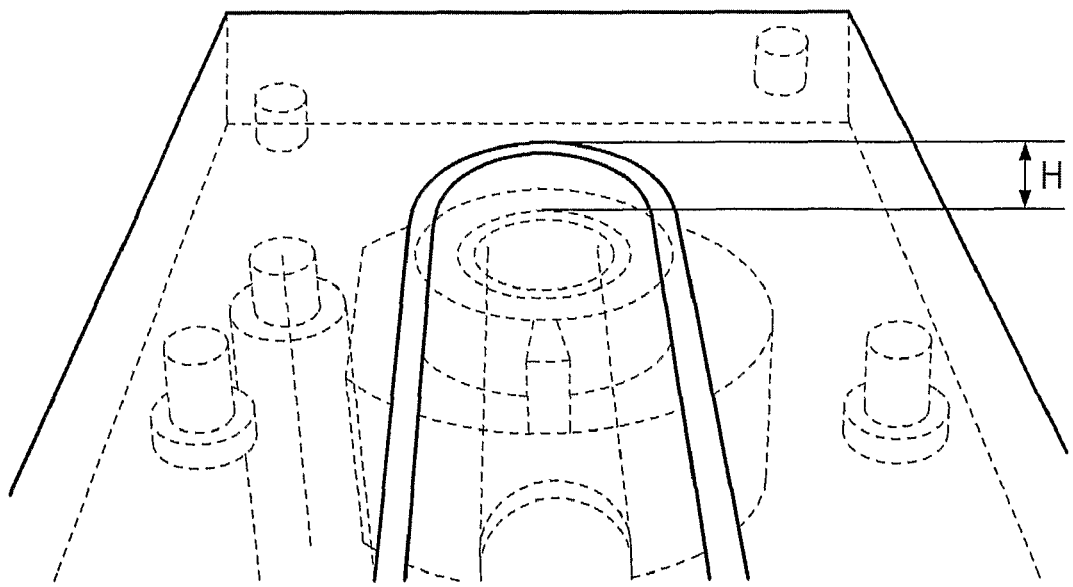

FIG. 1(j) shows a flow cell according to an embodiment of the invention having a flow channel having a length L of 60 mm, a width W of 10 mm and height H of 1 mm.

In some embodiments, a swirl pipe is provided upstream of the channel region 150 in order further to promote filling of the channel with fluid. A swirl pipe 170 according to one embodiment of the invention is shown in FIG. 2.

The swirl pipe 170 is in the form of a generally straight pipe section having one or more helical channels (or 'lobes') 172 formed in a surface of an inner wall 174 of the pipe. The helical channels 172 promote rotation of the fluid about a longitudinal axis of the pipe such that as the fluid enters the channel 150 of the housing 110, 120 substantially complete filling of the channel 150 with fluid occurs.

Figure 2:
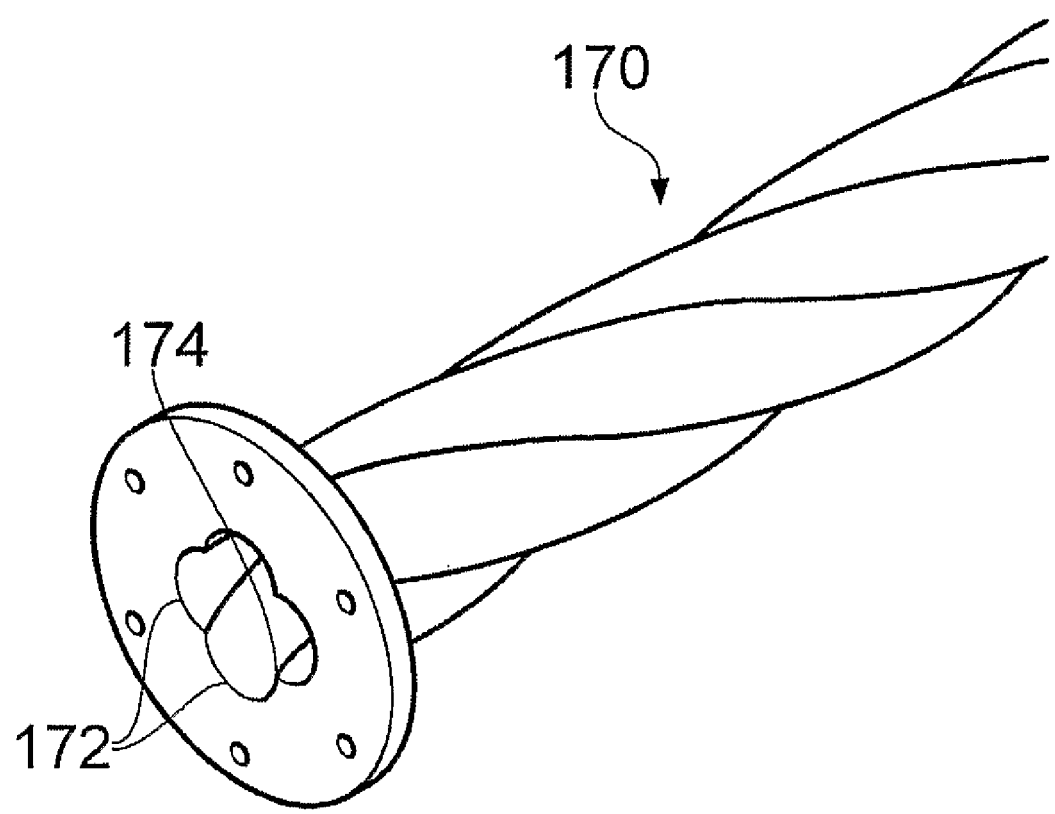
FIG. 2 shows a swirl pipe for use in some embodiments of the invention.

In the embodiment of FIG. 2, the swirl pipe 170 is provided with four channels 172 in sidewalls of the pipe 170. Other numbers of channels are also useful. The channels of the pipe 170 of FIG. 2 are generally semicircular in cross-section. Other channel shapes are also useful.

In use, the housing of FIG. 1 is optionally connected at an inlet 112, 122, 112A to an outlet 174 of the swirl pipe 170. Fluid is passed through the swirl pipe 170 and into the channel 150 of the housing.

In use, the piezoelectric crystal 140 is caused to oscillate at a resonant frequency $F_r$ and a difference $\Delta F_r$ between the resonant frequency $F_r$ and a reference frequency are measured. Optionally, $\Delta F_r$ may be measured as a function of time.

The reference frequency is generally the resonant frequency of the crystal 140 in air at room temperature and standard atmospheric pressure. Other conditions may be used in which to generate a reference frequency. For example, in some embodiments the reference frequency is the resonant frequency of the crystal when in contact with water.

Some embodiments of the invention are configured to measure yield stress of a fluid passing along the channel since the present inventors have discovered that the value of $\Delta F_r$ is proportional to a yield stress of a fluid.

Apparatus according to some embodiments of the invention can be calibrated by passing a plurality of fluids having one or more different respective rheological characteristics along the channel in a sequential manner and measuring $\Delta F_r$ for each fluid under either flow or no-flow conditions. A plurality of calibration values of $\Delta F_r$ may thereby be obtained.

It will be appreciated that cleaning of the exposed surface of the piezoelectric crystal may be required prior to exposure of the crystal to each respective fluid.

In some embodiments of the invention values of yield stress of the respective fluids (measured using an independent yield stress measurement technique) and corresponding values of $\Delta F_r$ are stored in a memory of the apparatus for use in calculating values of yield stress of fluids for future measurements of $\Delta F_r$ of a fluid.

In some embodiments the calculation of the value of the yield stress of a given fluid based on a measurement of frequency difference $\Delta F_r$ is calculated by an interpolation or extrapolation process with respect to calibration values. By calibration value is meant a value of $\Delta F_r$ for a known value of yield stress of the fluid obtained from pre-calibration of the instrument.

In some embodiments the calculation of the value of the yield stress is performed using an algorithm determined from pre-calibration of the instrument.

It will be appreciated that in some embodiments of the invention, the greater the number of calibration values available the greater the accuracy with which yield stress of a given fluid can be calculated.

Figure 3:
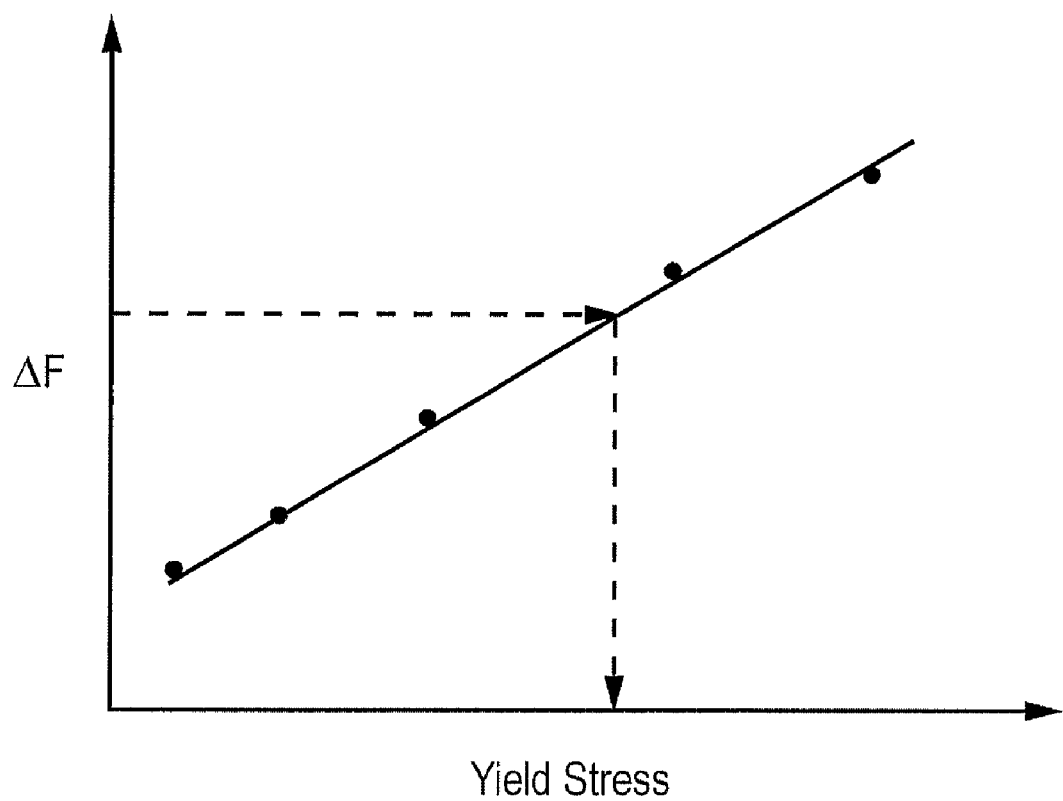
FIG. 3 is a raw data plot of change in resonant frequency $\Delta F_r$ as a function of yield stress of a particulate fluid.

Preliminary investigations suggest that the change in resonant frequency of the crystal of the apparatus is dependent on particle size, shape, density and porosity. A typical calibration curve for apparatus according to an embodiment of the invention is shown in FIG. 3, where values of $\Delta F_r$ of different fluids are plotted as a function of yield stress of the respective fluids.

Some embodiments of the invention have a piezoelectric crystal formed from an AT-cut quartz crystal coated in gold. Other coating materials are also useful, such as silica or platinum. In some embodiments the crystal has a resonant frequency in air of around 5 MHz at room temperature and standard atmospheric conditions. Crystals having other resonant frequencies are also useful.

By way of example, in one investigation an AT-cut crystal coated in both gold and platinum was used in apparatus according to an embodiment of the invention to measure yield stress of fluids containing some common compounds having a range of different yield stresses.

From values of $\Delta F_r$ and corresponding values of yield stress obtained, a relationship between frequency change and yield stress for fluids containing each compound was determined by a linear fit of the data. Scatter was present in the data due at least in part to the fact that the signal response is found to vary as a function of physical characteristics of the particles such as particle size and shape, and these were not necessarily uniform in the fluids tested in this example. The results of the investigation are shown in FIG. 4.

The data in respect of fluids containing the different compounds can be combined to provide a 'universal' relationship between frequency change and yield stress for any of the fluids. One such universal relationship for this investigation may be stated as follows for the given ranges:

(1 Pa-10 Pa) Yield stress (Pa)=$(\Delta F+824)/12.82$ (10 Pa-500 Pa) Yield stress (Pa)=$(\Delta F+1137)/2.97$ It will be appreciated that alternative functions relating the change in frequency to the yield stress of the fluid may be developed.

In some embodiments of the invention, calibration of a given instrument is performed by the manufacturer of the apparatus, the apparatus being ready for measurement of fluid yield stress substantially as-delivered to an end user, without a requirement to calibrate the apparatus. In some embodiments a set of calibration values for a given product type are substantially the same for each product of that type.

In some embodiments of the invention a housing according to the embodiment of FIG. 1 or variations thereof is incorporated in a production facility of a factory for monitoring yield stress of fluid passing along a pipe or other channel. In some embodiments, the apparatus is configured to generate an alert in the event that a yield stress of a fluid is greater than or less than a predetermined range of acceptable values of yield stress. For example, in the case of a facility producing a food sauce, the apparatus may be configured to generate an alert or modify a portion of a production process in the event that values of a measured parameter of the sauce (such as for example the yield stress, solids concentration and/or viscosity) is no longer within an acceptable range.

Figure 5:
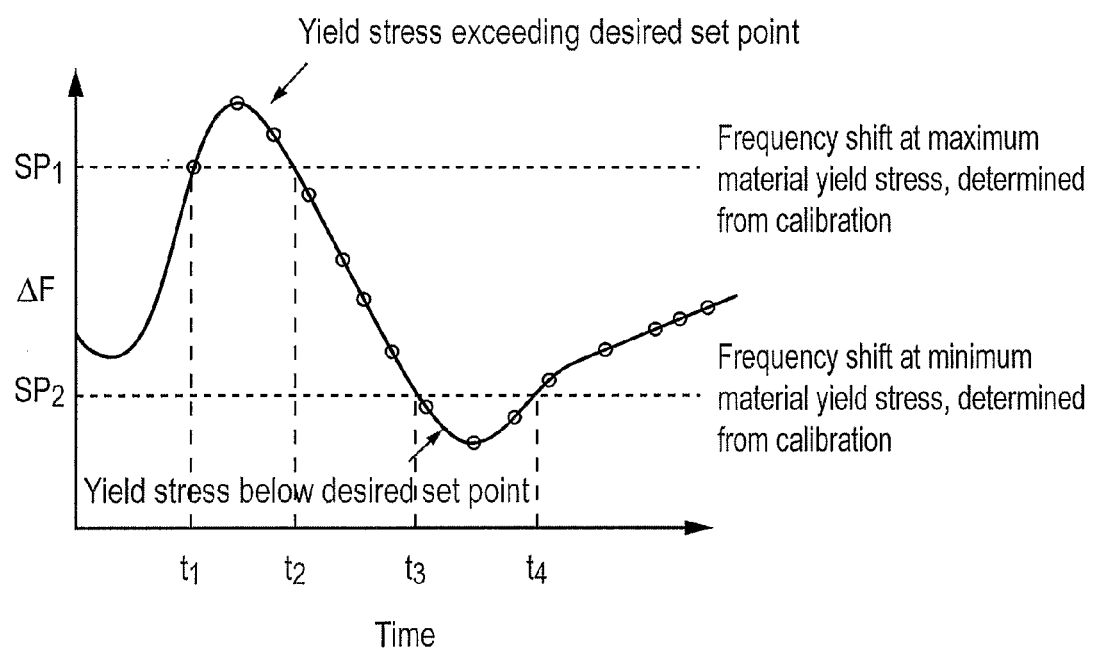
FIG. 5 is an example of a plot of measurements of $\Delta F_r$ as a function of time in a system according to an embodiment of the invention showing a variation in yield stress of the fluid made under zero-flow conditions as a function of time.

FIG. 5 shows an example of an output of a fluid analyser as a function of time in an interrupted flow online yield stress measurement apparatus suitable for such an application.

It can be seen from the plot of FIG. 5 that over the time period represented in the plot the yield stress of the fluid was found to vary as a function of time. The yield stress exceeded an upper critical set point value $SP_1$ between time $t_1$ and $t_2$, and fell below a lower critical set point value $SP_2$ between time $t_3$ and $t_4$. It is to be understood that measurement of yield stress may be used in a feedback loop to control processing or manufacture of the fluid, for example by adjusting a composition of the fluid or any other suitable parameter.

In some embodiments of the invention the flow of fluid through the apparatus is stopped when it is required to measure yield stress. Once a yield stress measurement has been made, fluid flow is recommenced. This is because more accurate measurements of yield stress are typically obtained under zero-flow or substantially zero-flow conditions.

Thus, in some embodiments of the invention the apparatus is installed in a secondary flow line of a production facility that can be isolated from one or more primary flow lines of the facility. The apparatus is fed a supply of fluid such that the crystal is entirely covered with fluid, and flow of fluid across the crystal is arrested. A yield stress measurement is then made. In some embodiments of the invention a yield stress data point is obtained at intervals of around 10 seconds.

Once the apparatus has acquired a yield stress measurement the fluid in the secondary flow line may be either fed back into the primary flow line or otherwise disposed of.

FIG. 6 shows plots of data obtained from apparatus according to embodiments of the present invention.

Figure 6A:
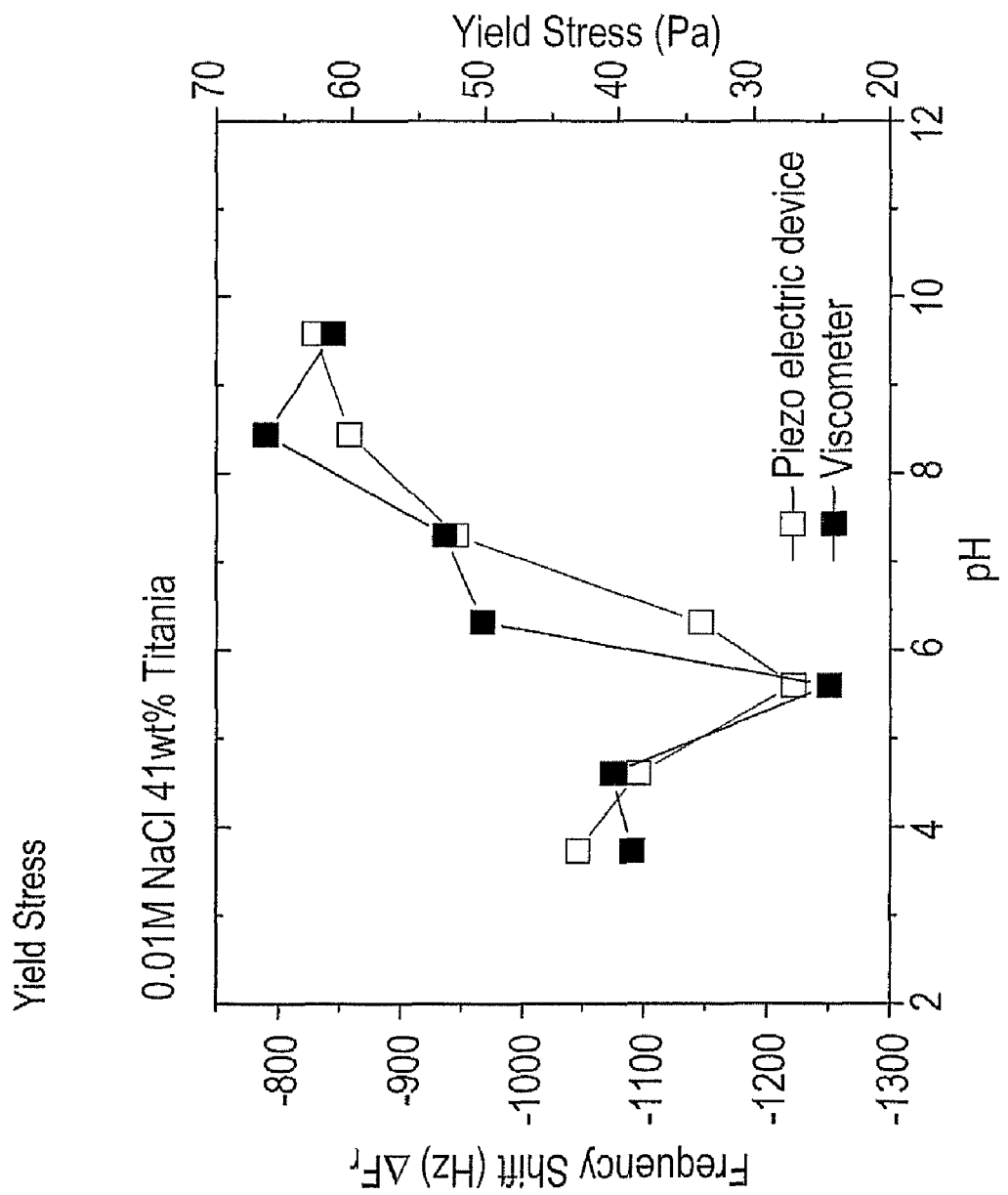
FIG. 6 (a) to (h) shows a series of plots of frequency shift as a function of a given parameter for a series of fluids.

FIG. 6(a) shows a plot of frequency shift $\Delta F_r$ as a function of pH for a 0.01M aqueous solution of NaCl with 41 wt % Titania for a piezoelectric device according to an embodiment of the invention. Yield stress measurements obtained using a conventional viscometer are shown in the plot for comparison. It can be seen that the respective plots are highly correlated.

Figure 6B:
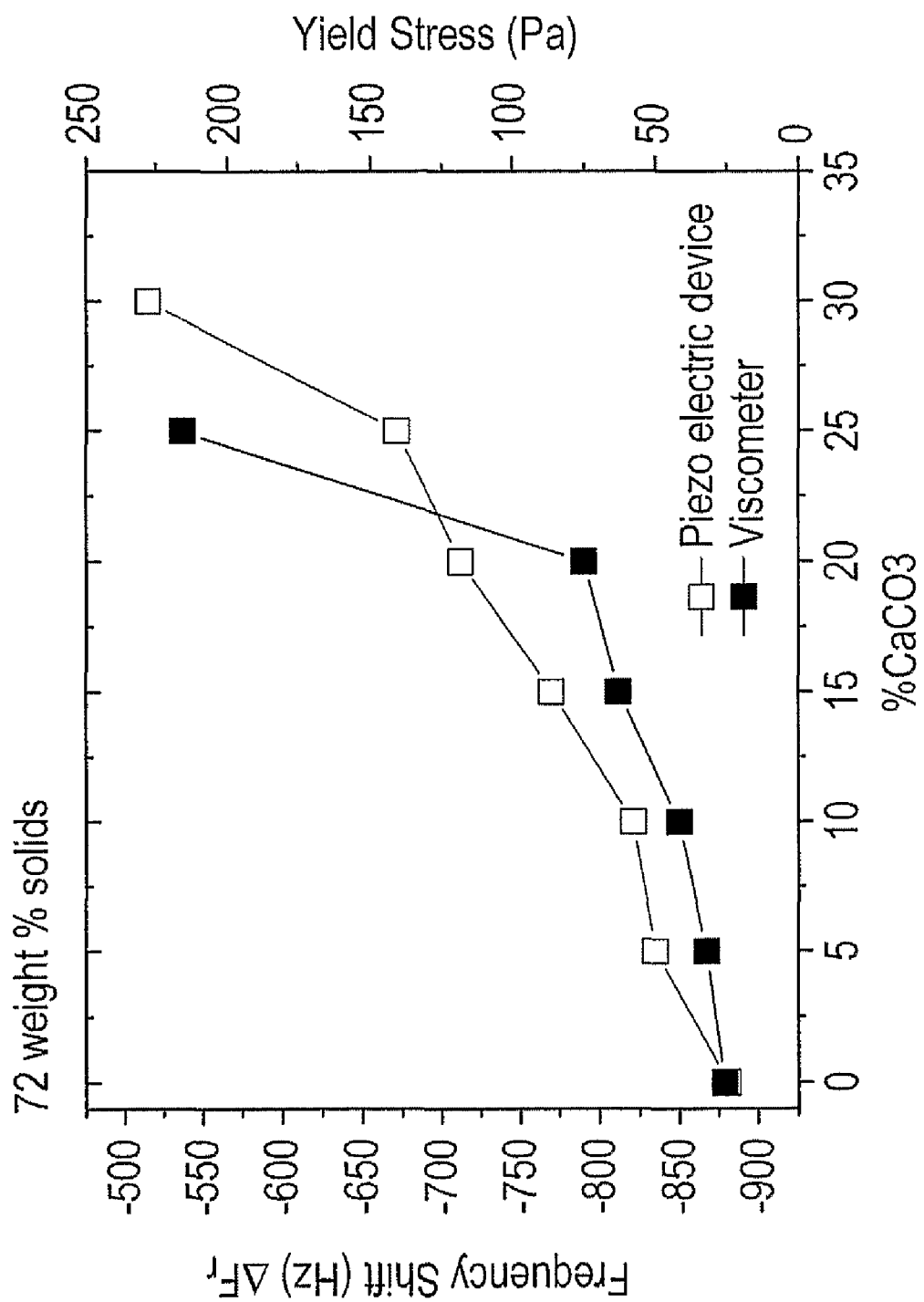

FIG. 6(b) is a plot of frequency shift $\Delta F_r$ as a function of weight percent $CaCO_3$ in a mixture of $CaCO_3$, silica and water obtained using a similar piezoelectric device to that used to obtain the plot of FIG. 6(a). The mixture was arranged to have a total solids concentration of 72 weight percent.

Yield stress measurements obtained using a conventional viscometer are shown in the plot for comparison. Again it can be seen that data from the two different types of apparatus are highly correlated.

Figure 6C:
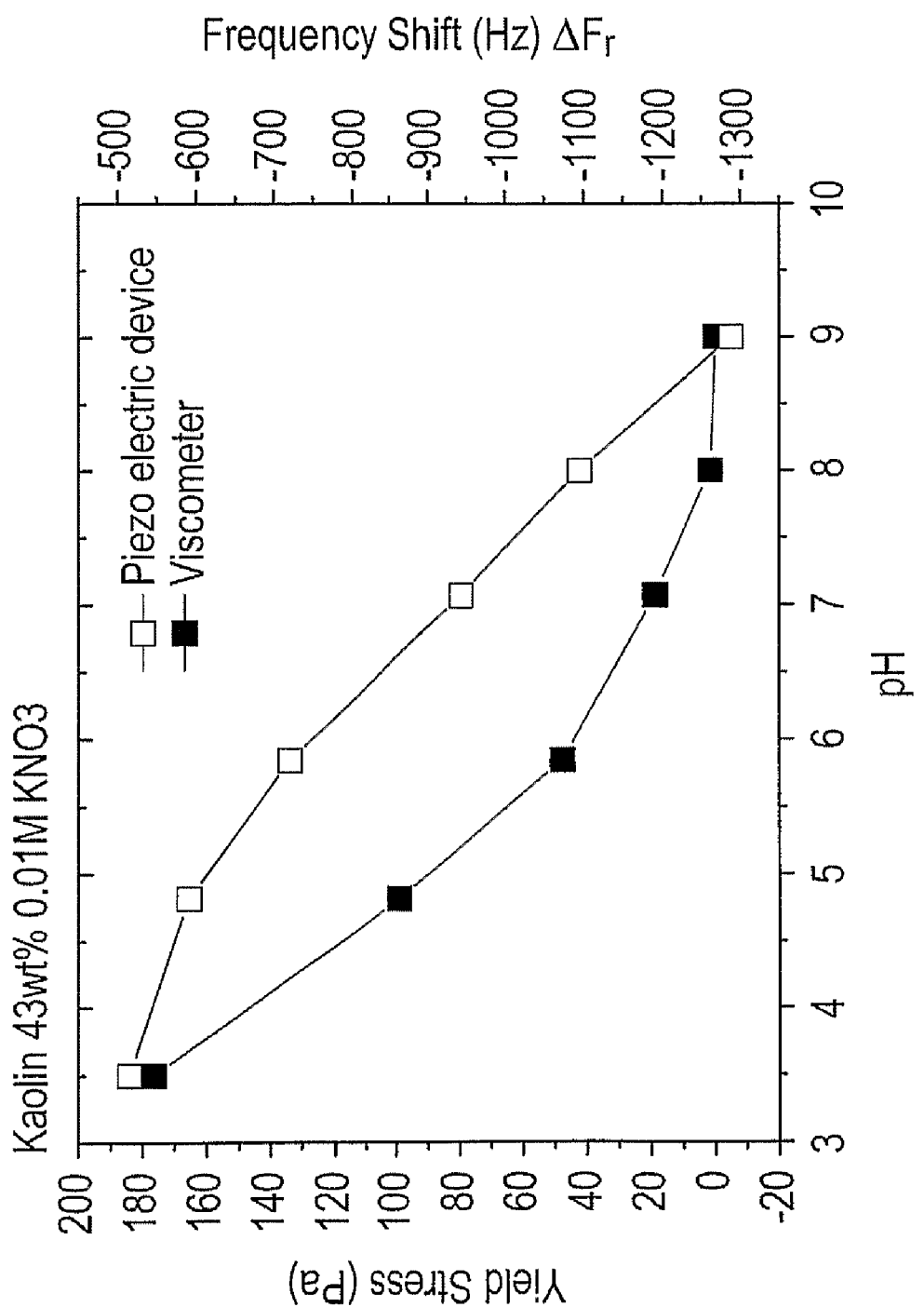

FIG. 6(c) shows a plot of frequency shift $\Delta F_r$ as a function of pH for an aqueous solution of 0.01M KNO3 with 43 weight % Kaolin obtained using a similar piezoelectric device to that used to obtain the plots of FIGS. 6(a) and (b). Again, yield stress measurements obtained using a conventional viscometer are shown in the plot for comparison and the respective plots are highly correlated.

Figure 6D:
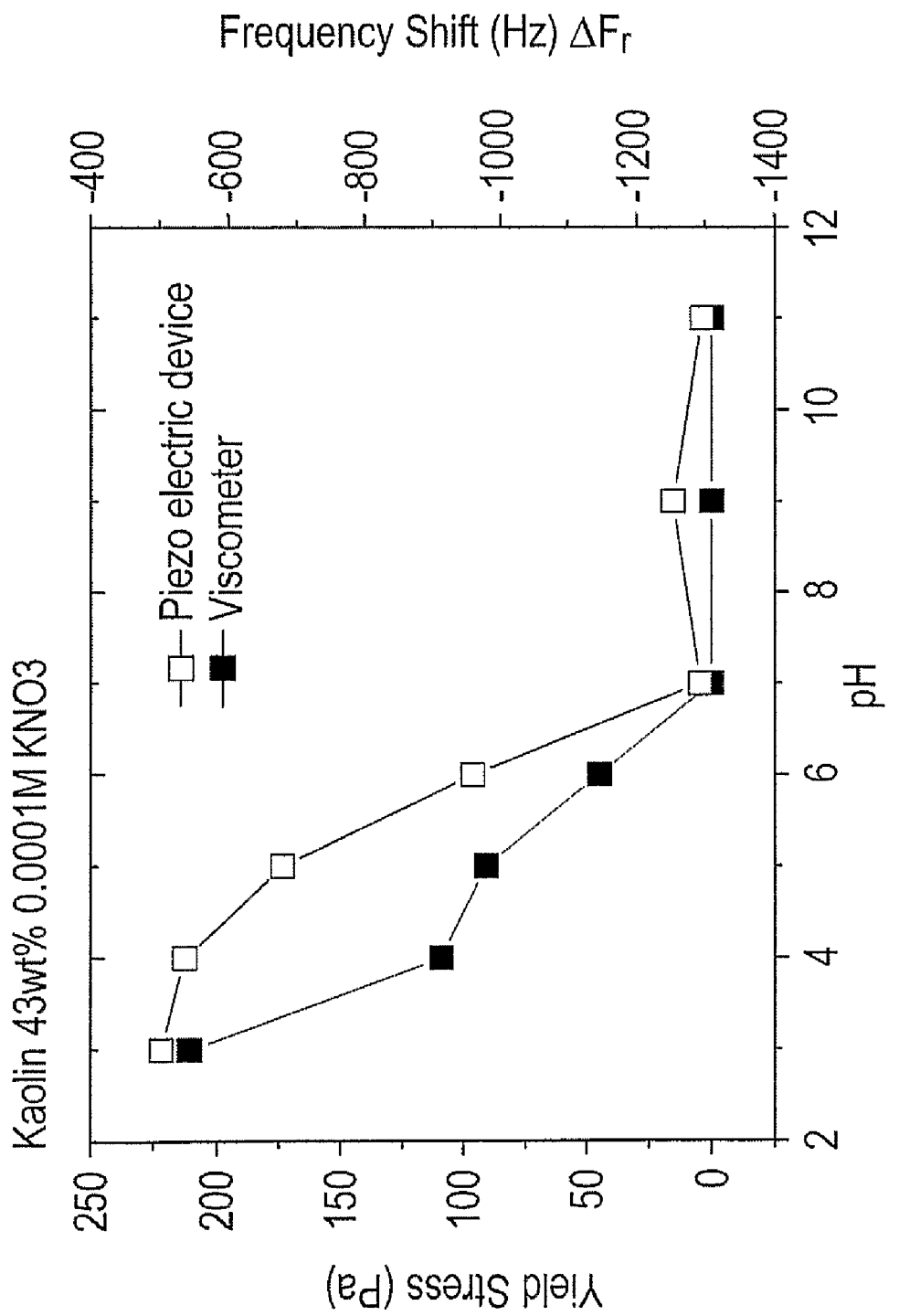

FIG. 6(d) is a similar plot to that of FIG. 6(c) except that the data was obtained by measuring an aqueous solution of 0.0001M KNO3 with 43 weight % Kaolin.

Figure 6E:
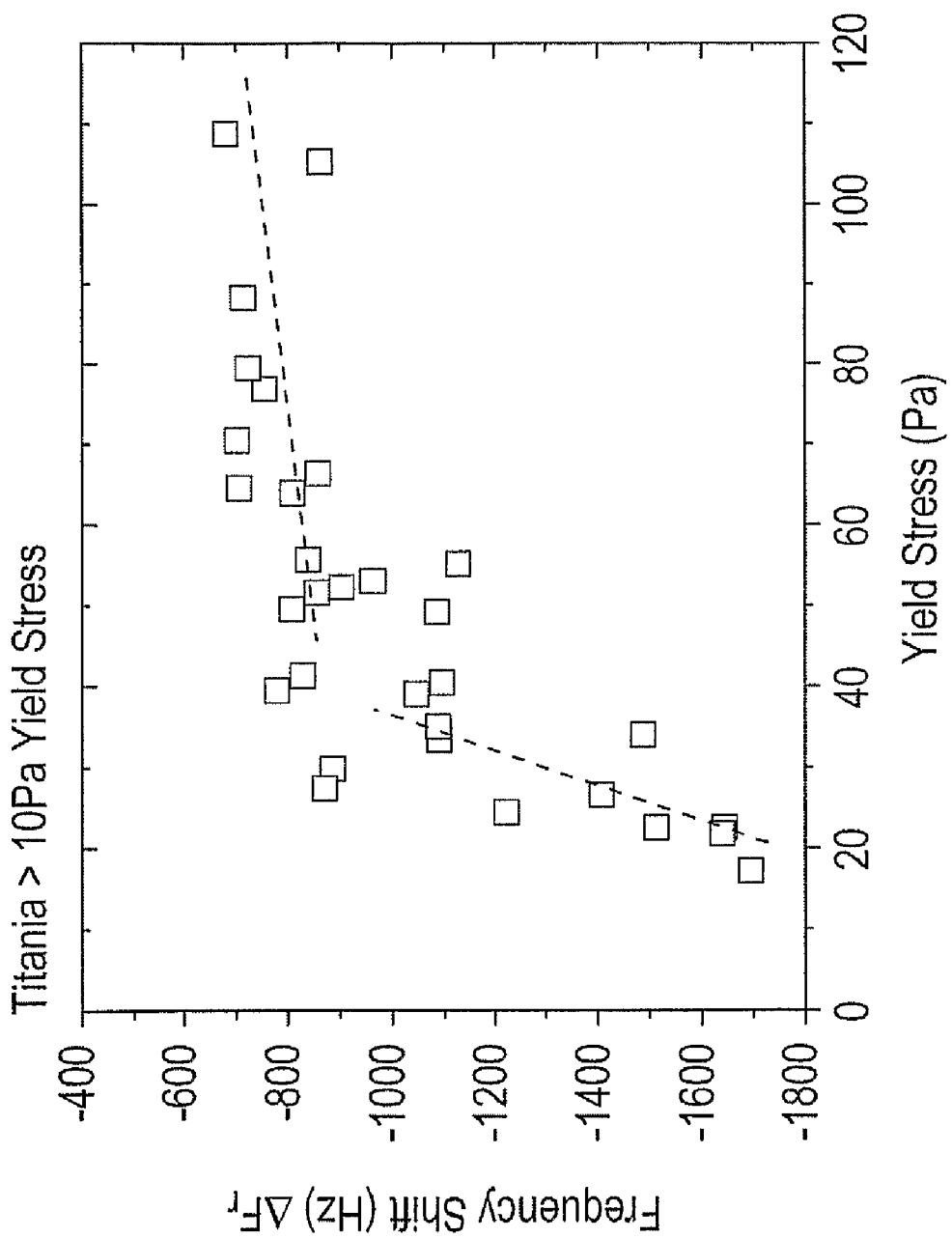
Figure 6F:
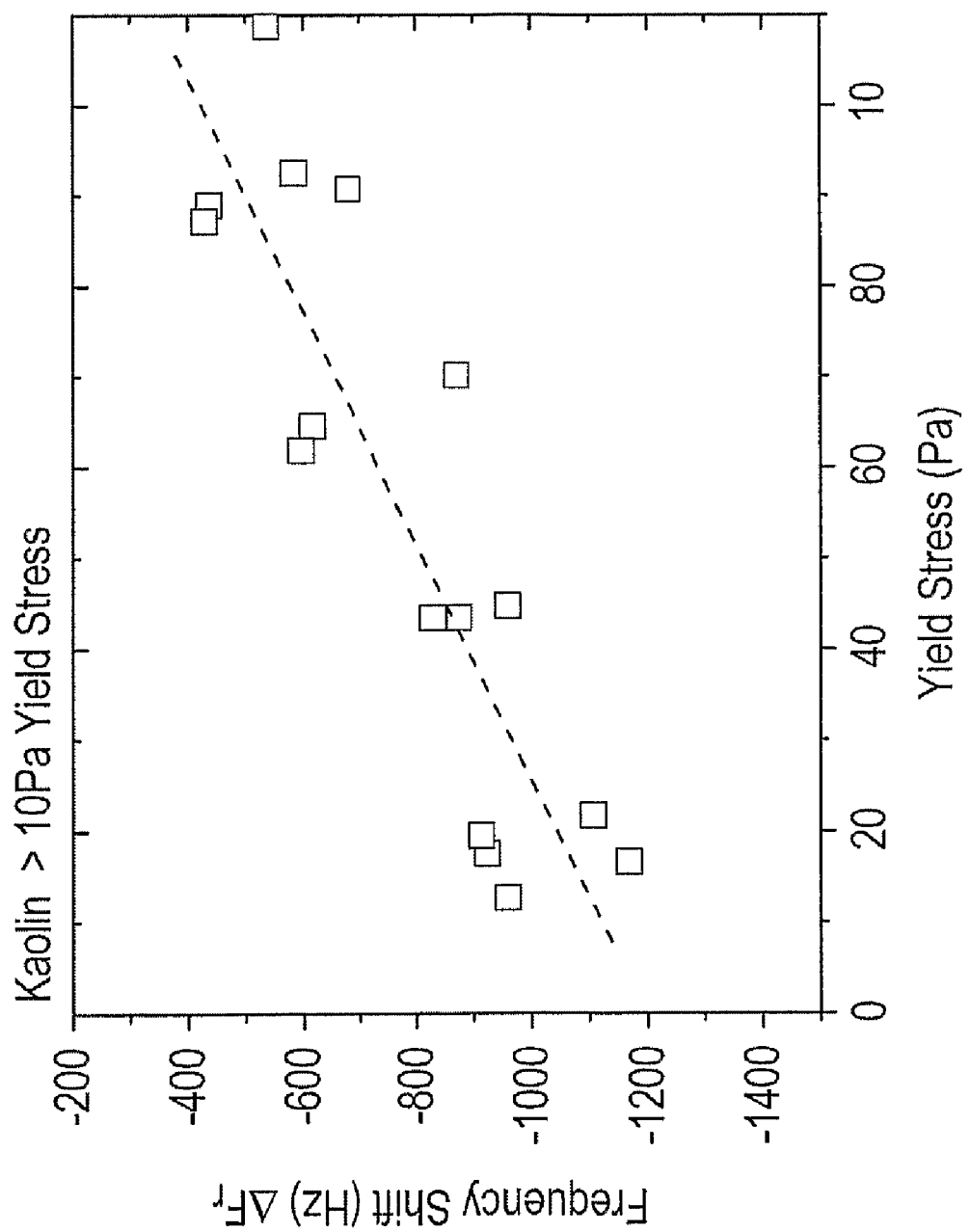
Figure 6G:
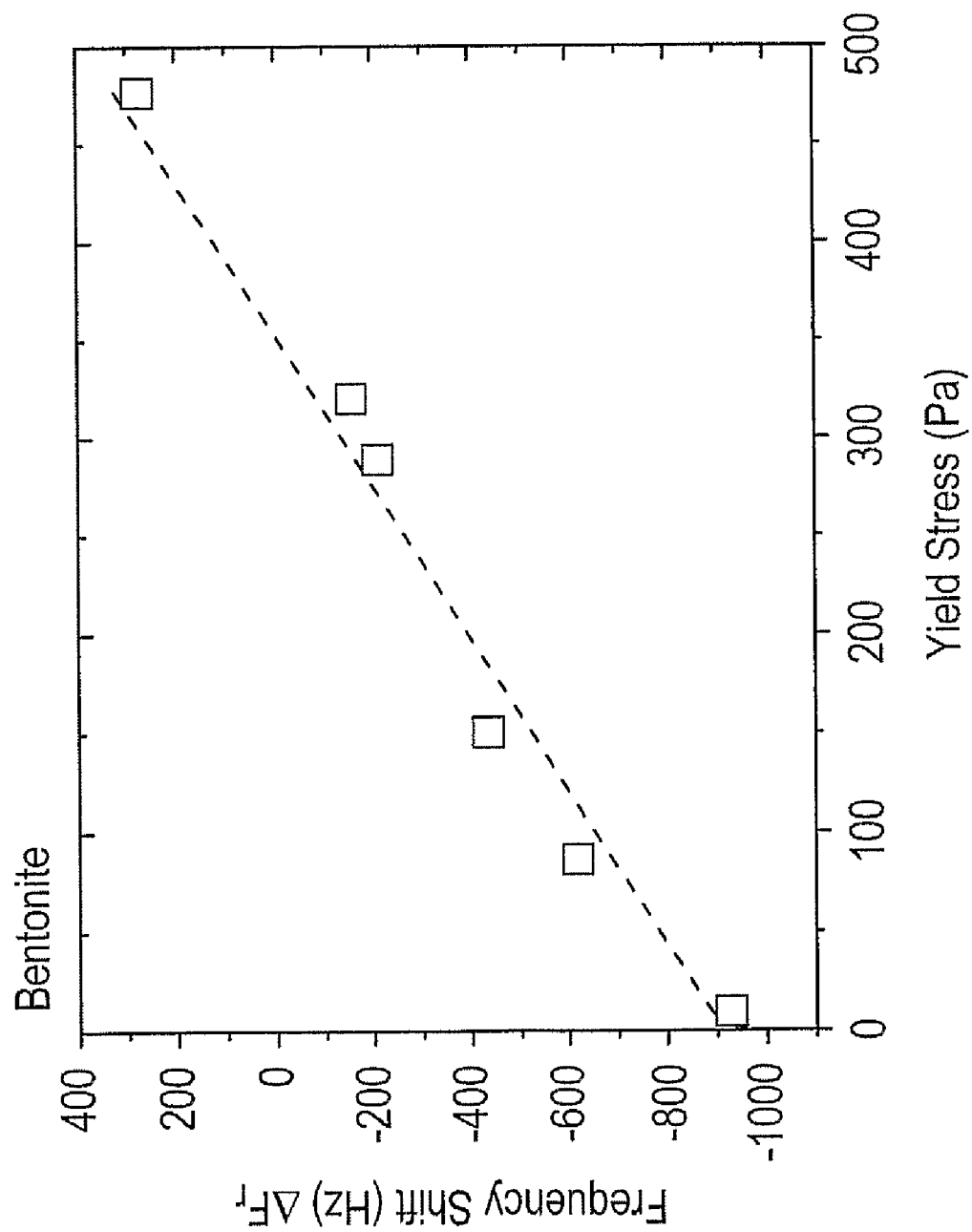
Figure 6H:
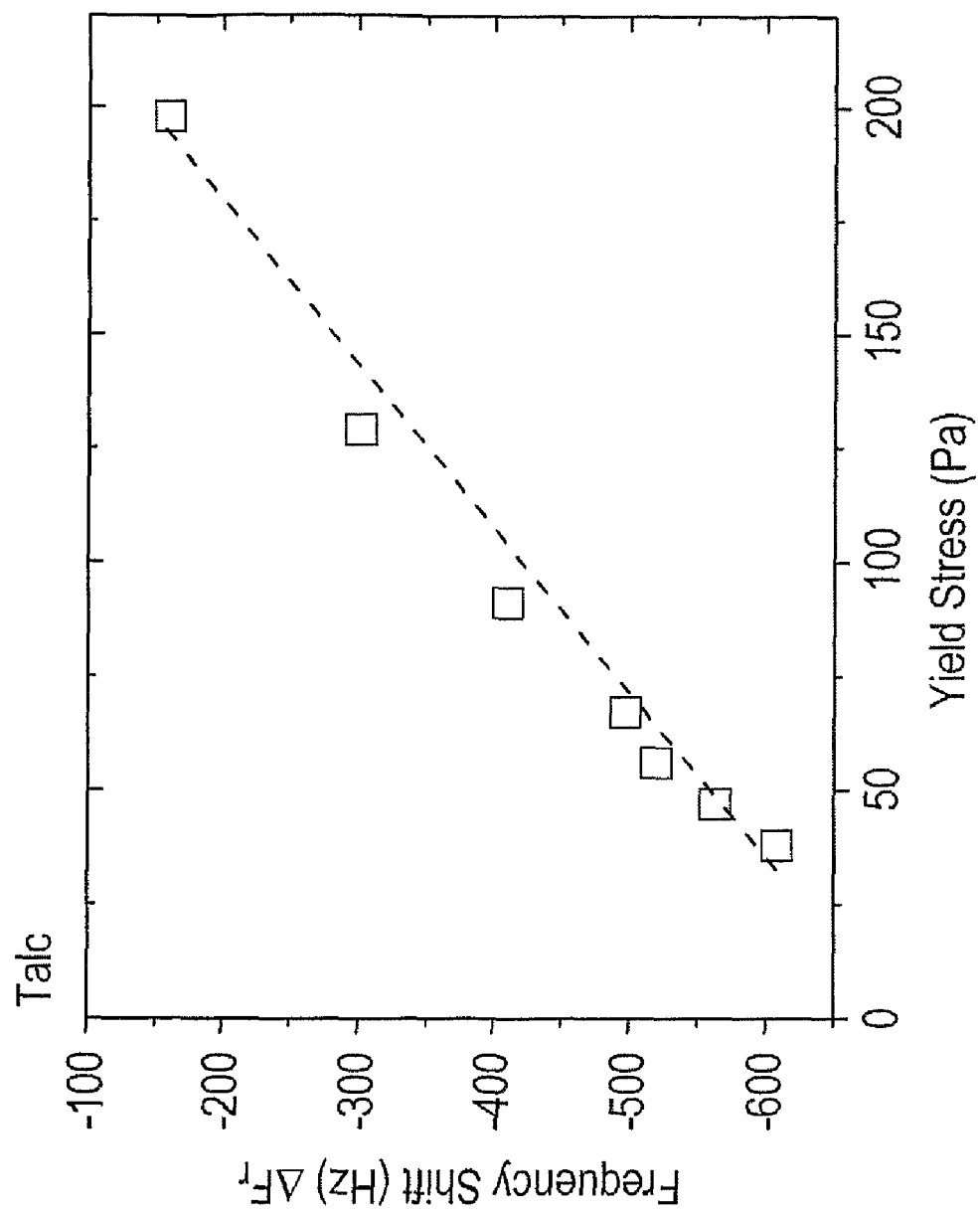

FIG. 6(e) shows a plot of frequency shift $\Delta F_r$ as a function of yield stress for titania particles in water at an amount for which the yield stress exceeds 10 Pa. FIGS. 6(f), (g) and (h) show similar plots for kaolin, bentonite and talc particles in water, respectively.

Figure 7:
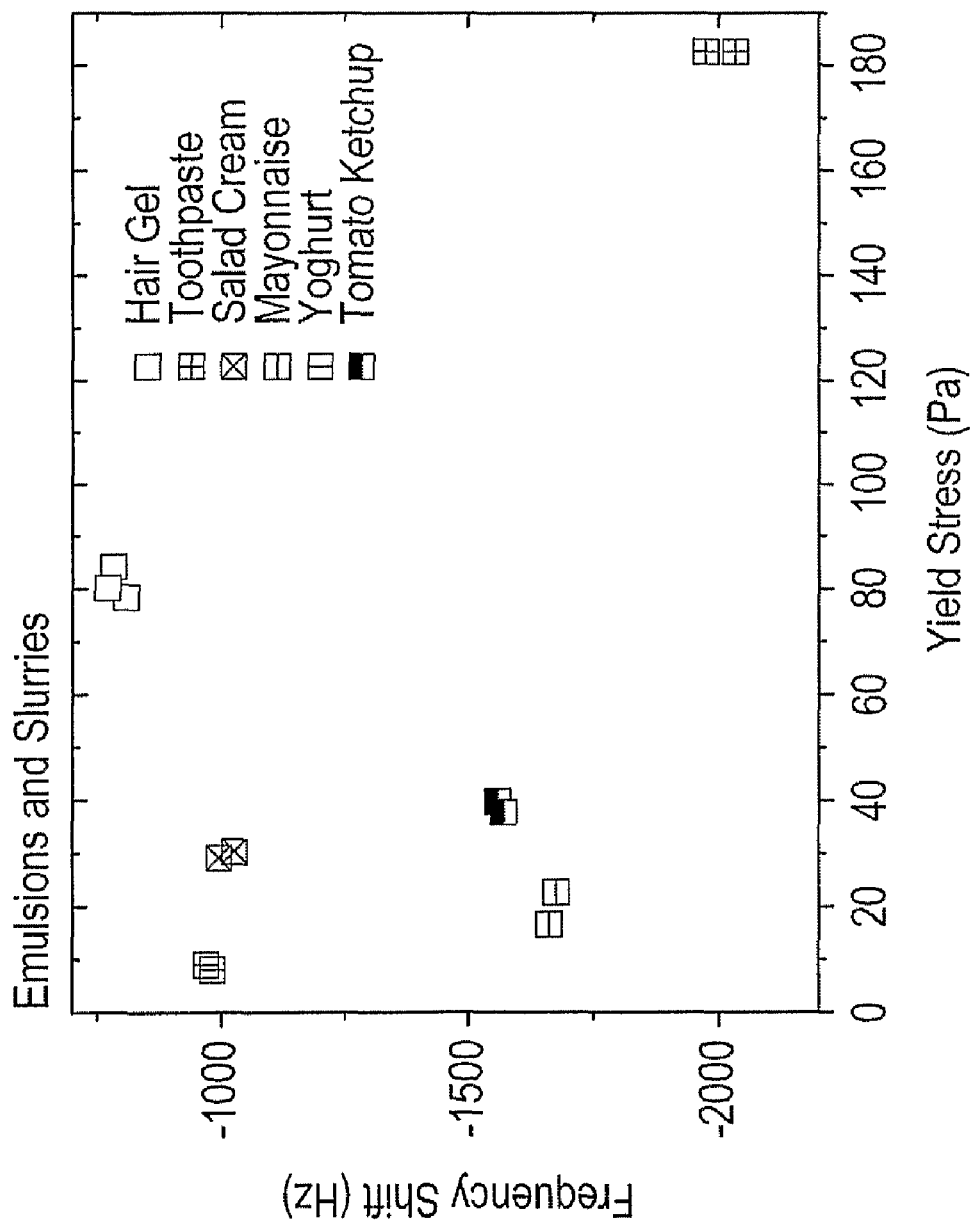
FIG. 7 is a plot of frequency shift as a function of yield stress for a series of domestic fluids.

FIG. 7 shows a plot of frequency shift $\Delta F_r$ as a function of yield stress for a series of measurements of six domestic test fluids (being different respective domestic fluid products)

using a similar piezoelectric device to that used to obtain the plots of FIG. 6. Between respective measurements made on a given test fluid the probe was removed from the fluid, cleaned in water to remove any fluid that remained on the device and then re-inserted into the fluid.

It can be seen that the repeated measurements of the same test fluid are highly correlated, and different types of domestic fluid product are well spaced apart on the plot of $\Delta F_r$ as a function of yield stress.

Figure 8A:
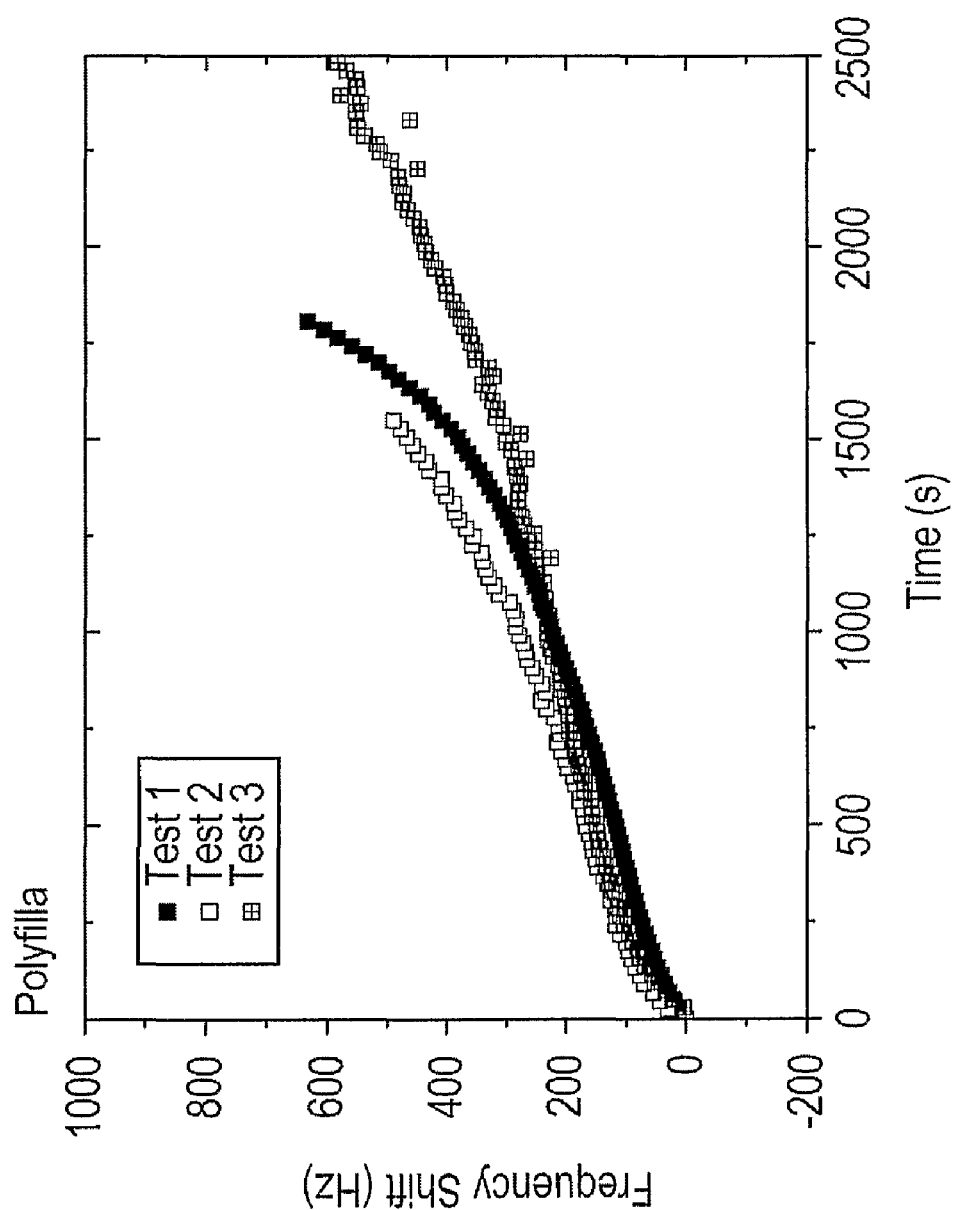
FIG. 8 is a plot of frequency shift as a function of time during curing of (a) three samples of a cellulose household filler material (Polyfilla®) applied to a surface; (b) a sample of Polyfilla® left to stand in a beaker and a sample of Polyfilla® applied to a surface and subjected to heating; and (c) two samples of gelatine.

FIG. 8 shows a plot of $\Delta F_r$ as a function of time for a piezoelectric device according to an embodiment of the invention in contact with a fluid that is in a process of curing. FIG. 8(a) shows data obtained during curing of three different samples of Polyfilla®.

Figure 8B:
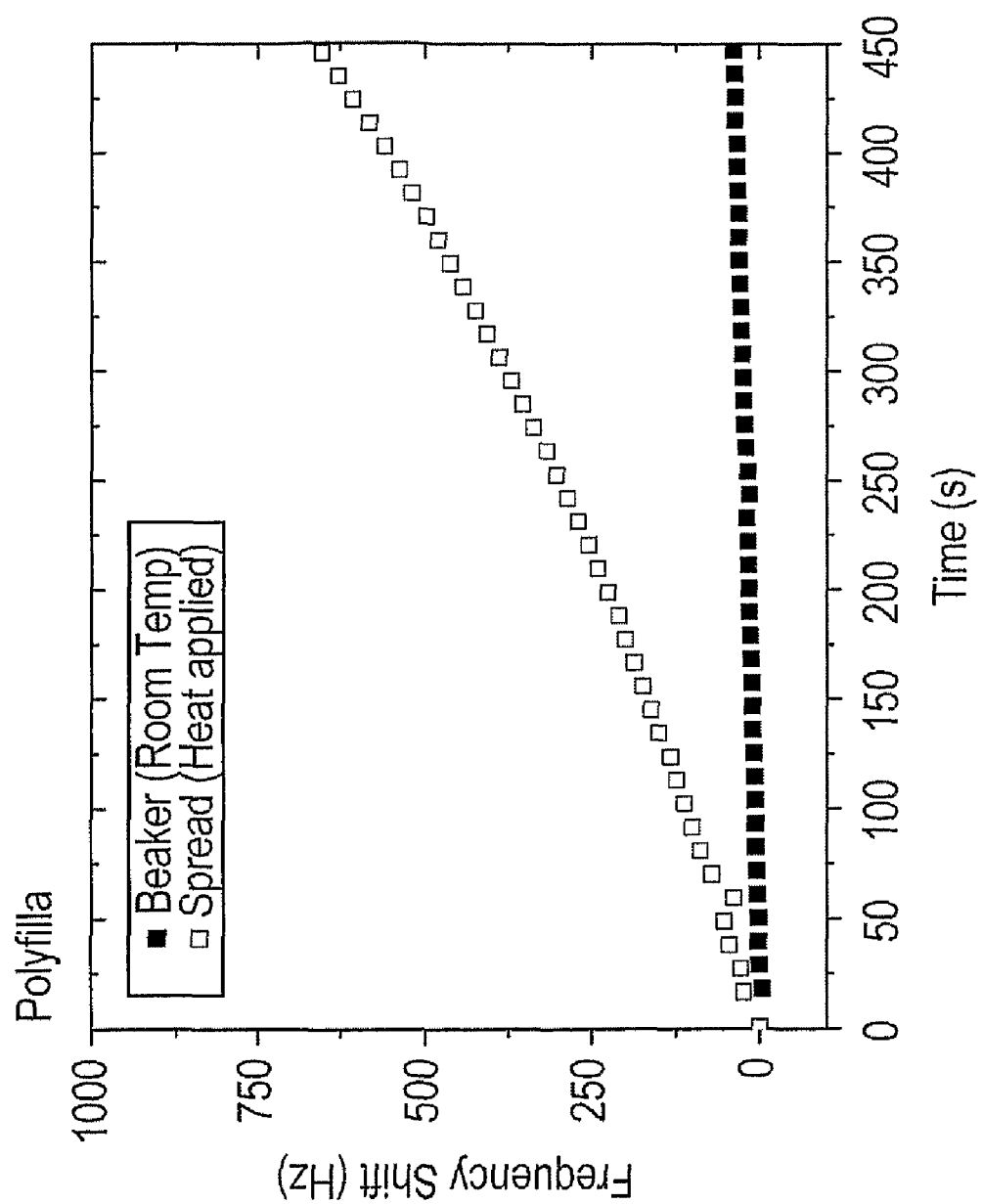

FIG. 8(b) shows data obtained during curing of a sample of Polyfilla® in a beaker held at room temperature (filled squares) and data obtained from a layer of Polyfilla® to which heat was applied to accelerate curing. It can be seen that the gradient of the plot of $\Delta F_r$ as a function of time is much steeper in the case of the sample in the form of a layer compared with that contained in a beaker indicating that curing occurred more quickly when the sample was spread to form a layer and heat applied.

Figure 8C:
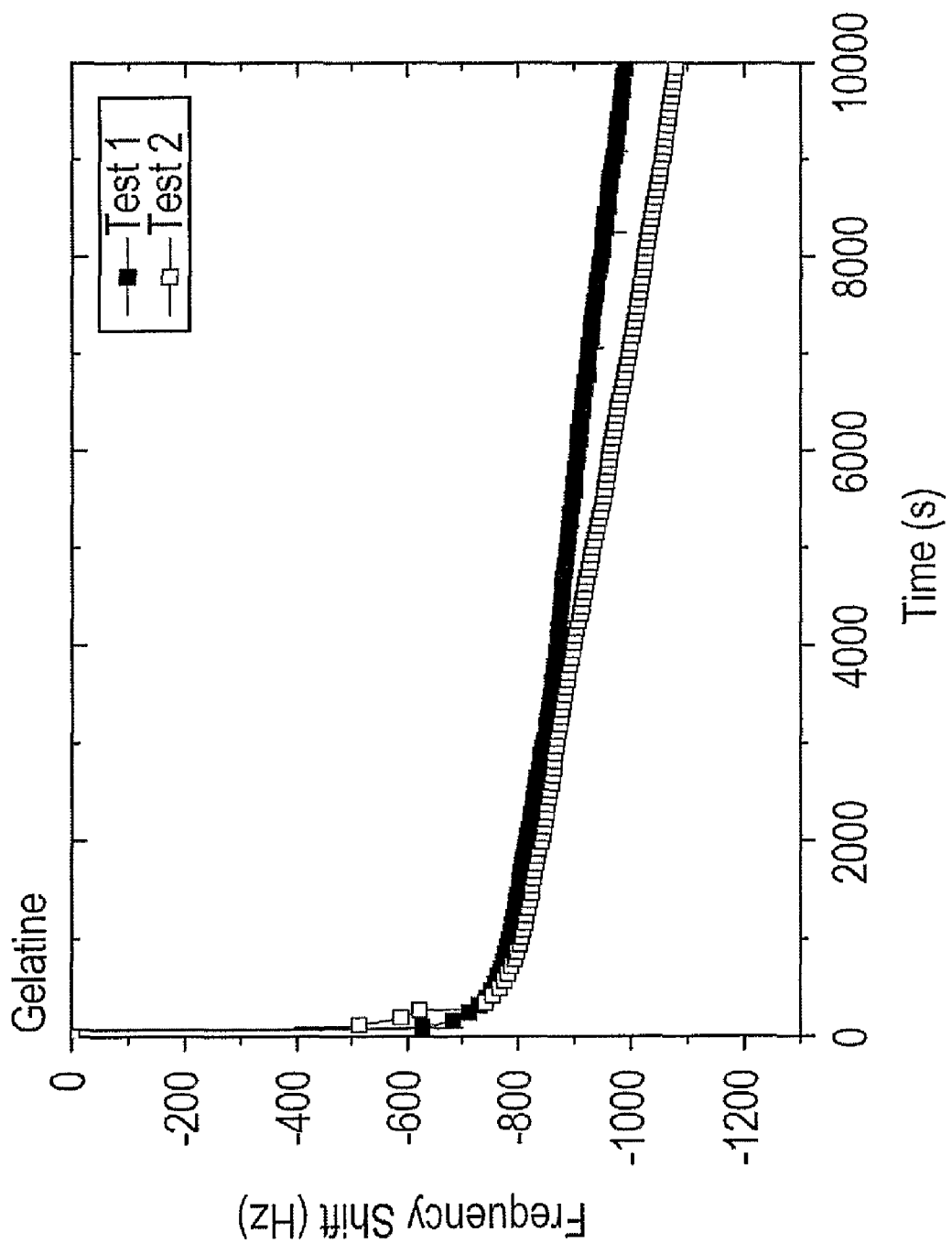

FIG. 8(c) shows a plot of resonant frequency as a function of time obtained during curing of two different samples of gelatine. It can be seen that a negative frequency shift occurs as curing proceeds.

Figure 9:
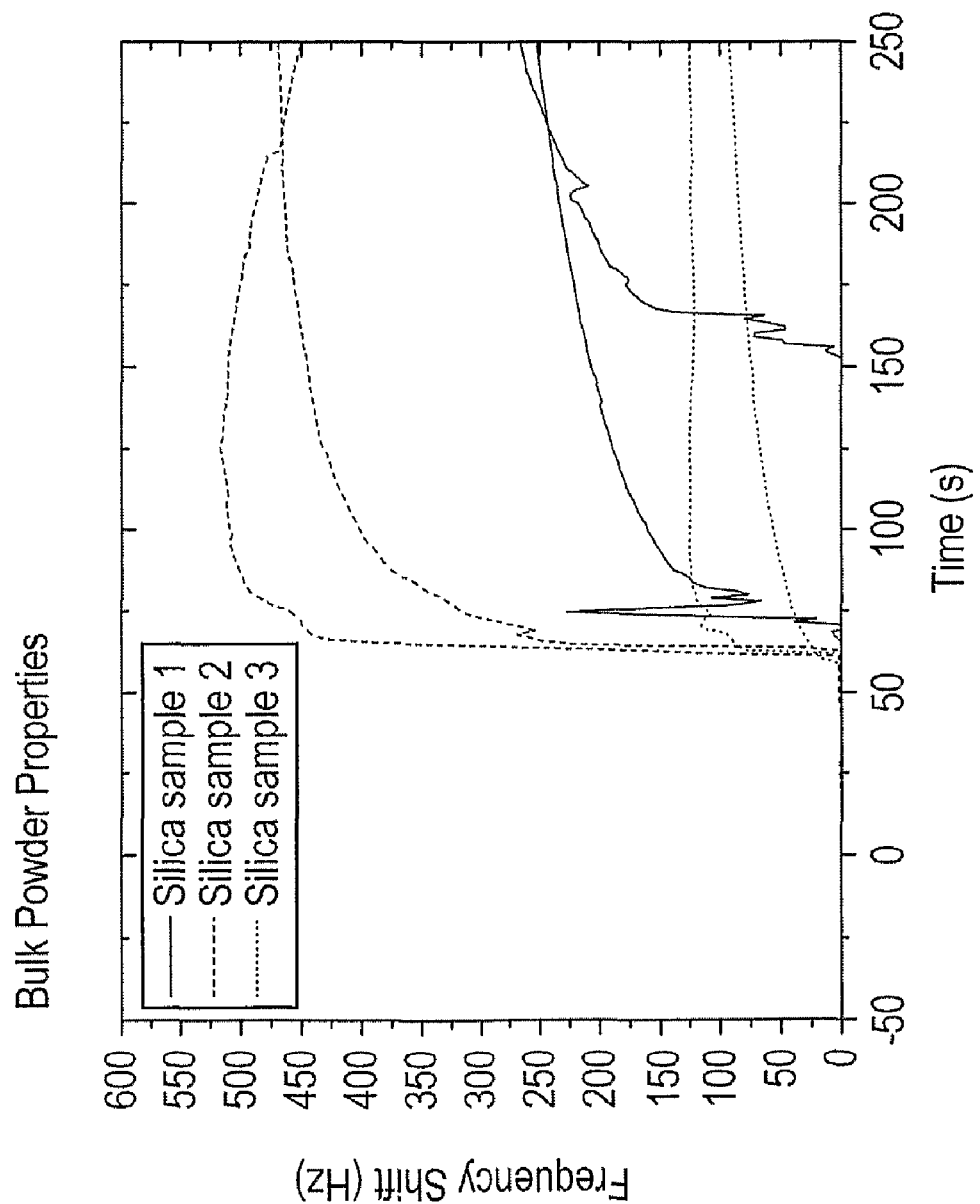
FIG. 9 is a plot of frequency shift as a function of time during immersion of a hand-held device according to an embodiment of the invention into three different bulk samples of a dry silica powder.

FIG. 9 shows a plot of $\Delta F_r$ as a function of time obtained by submerging a piezoelectric device according to an embodiment of the invention into three different samples of a silica material in the form of a dry powder. It can be seen that different frequency responses are observed when the device is submerged in the respective different samples. Thus it is to be understood that embodiments of the invention are useful for characterising the rheological of fluids in the form of dry powders as well as slurries, gels and other fluids as described above.

Data corresponding to two separate measurements on the same powder are shown in the plot. The data corresponding to the measurements can be seen to be reasonably well correlated.

Instead of or in addition to measuring yield stress of a fluid, determination of a solids concentration and/or a viscosity of a fluid can be made. The procedure is similar to that in respect of determining fluid yield stress, except that a calibration curve (or equation corresponding to a calibration curve) is first obtained from which frequency shift as a function of solids concentration (or viscosity) for the apparatus is determined using fluids of known solids concentration (or viscosity).

In the case of measurements of solids concentration or viscosity, no-flow conditions are not necessarily advantageous and continuous flow of fluid through the apparatus can be maintained. This is because in measuring these parameters bridging contact mechanics between particles are not being measured.

Measurement of solids concentration in a fluid is useful since not all fluids exhibit a shear yield stress.

Figure 10:
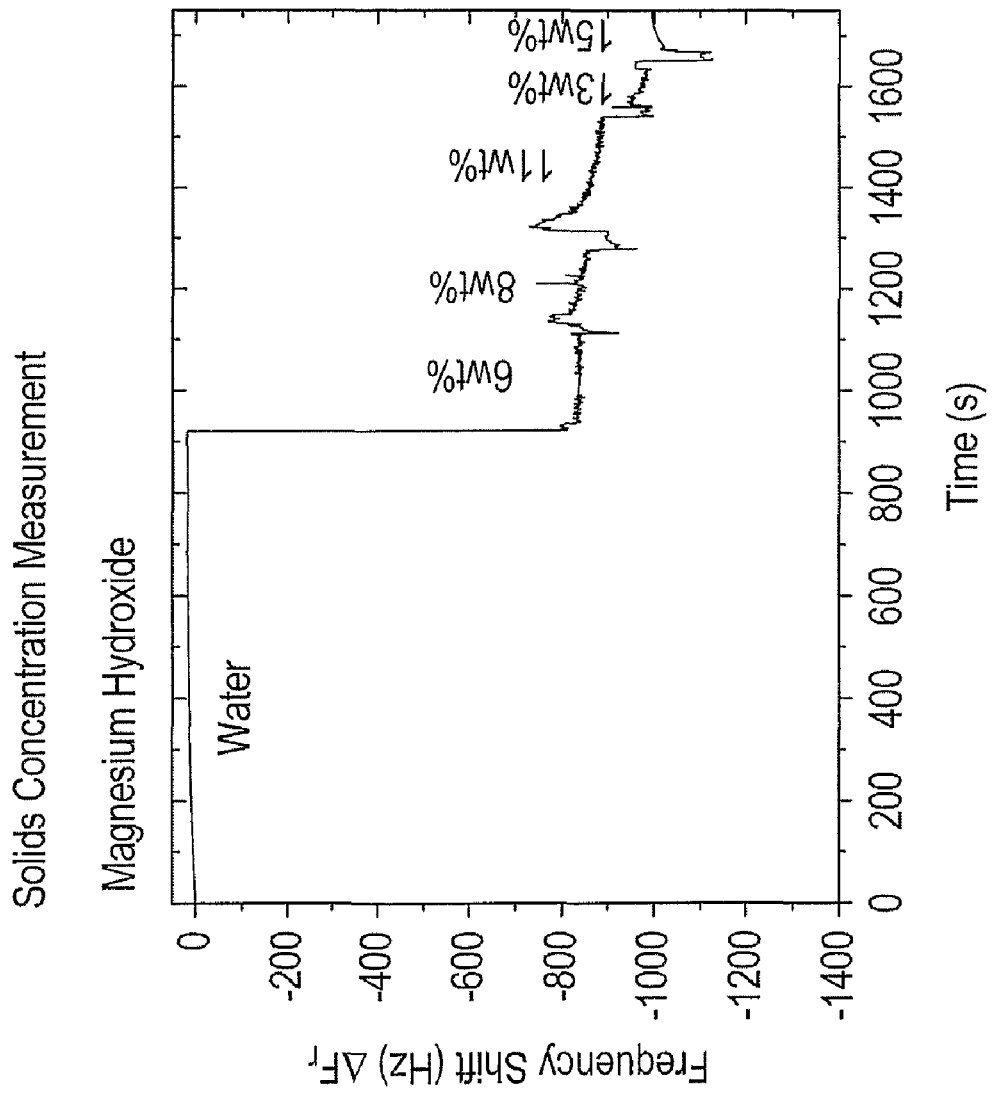
FIG. 10 is an example of a plot of $\Delta F_r$ as a function of time for a piezoelectric crystal of apparatus according to an embodiment of the invention in contact with a magnesium hydroxide fluid wherein the amount of magnesium hydroxide present in the fluid was increased as a function of time.

By way of example, FIG. 10 shows a plot of the change (or 'shift') in resonant frequency $\Delta F_r$ relative to a reference frequency of a piezoelectric crystal in a flow cell according to an embodiment of the invention.

For time t=0 to around t=900s the crystal was exposed to water to establish a calibration with respect to water, i.e. to determine the resonant frequency $F_r$ of the crystal in water. Increasing amounts of magnesium hydroxide were then added to the water forming a slurry which was pumped through the flow cell thereby to increase the solids concentration of the water. The amount of magnesium hydroxide added to the water (measured in weight percent) at various times is indicated in FIG. 10.

Figure 11:
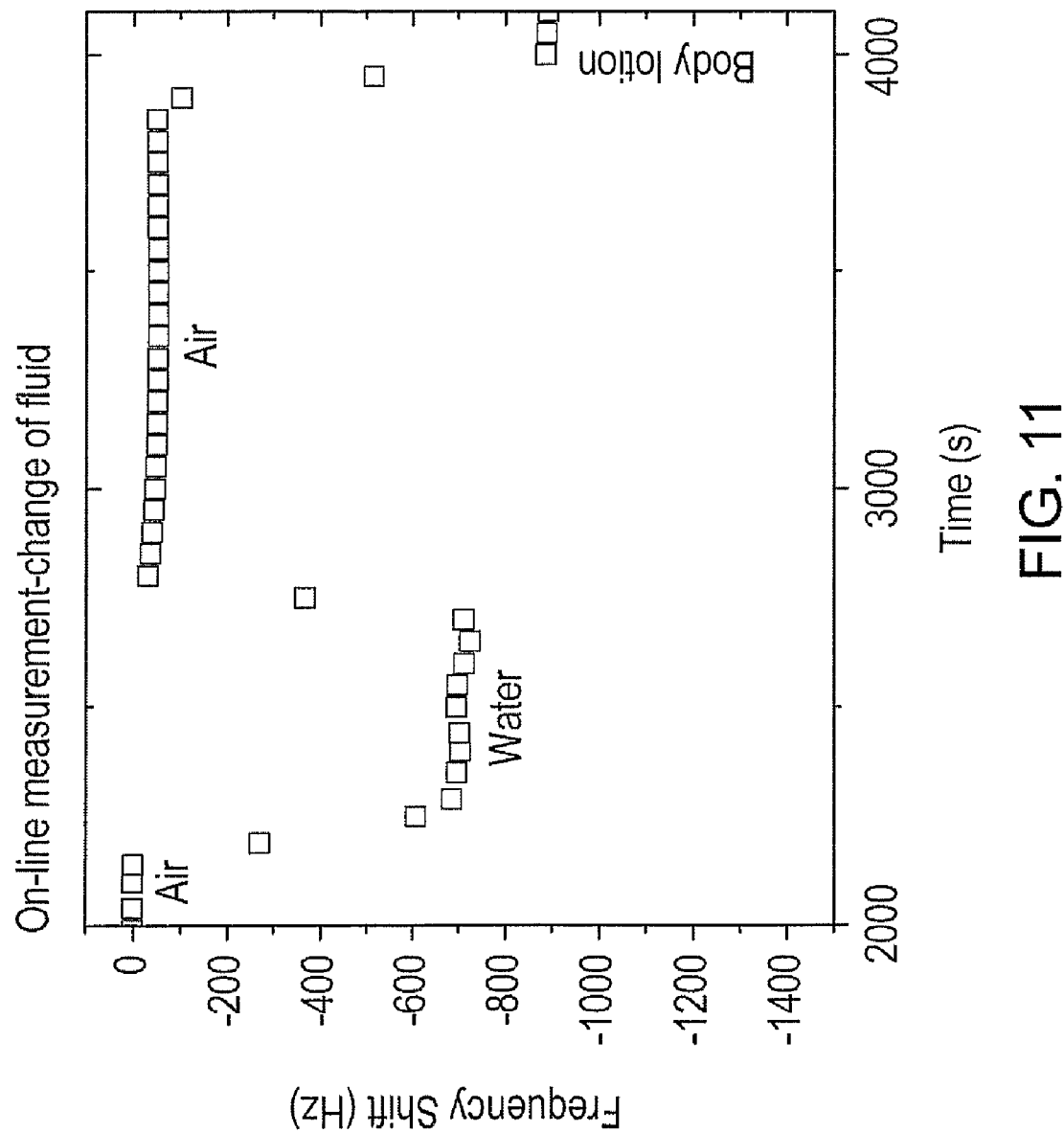
FIG. 11 shows a difference in resonant frequency $\Delta F_r$ as a function of time for a piezoelectric crystal of apparatus according to an embodiment of the invention having a channel through which fluid may flow and contact the crystal when water and subsequently body lotion were passed through the channel.

FIG. 11 shows a plot of frequency shift $\Delta F_r$ as a function of time for a piezoelectric crystal in an 'on-line' flow cell as different fluids are passed through the flow cell.

Initially the piezoelectric crystal is exposed to air. Subsequently at time t~2200s the crystal was exposed to water, at time t~2750s the crystal was again exposed to air and then at time t~4000s the crystal was exposed to body lotion. It can be seen that different values of frequency shift $\Delta F_r$ are observed for different fluids in contact with the piezoelectric crystal. Thus, the piezoelectric crystal enables identification of a fluid to be performed and characteristics of the fluid to be determined in real time as fluid passes through the flow cell.

Figure 12:
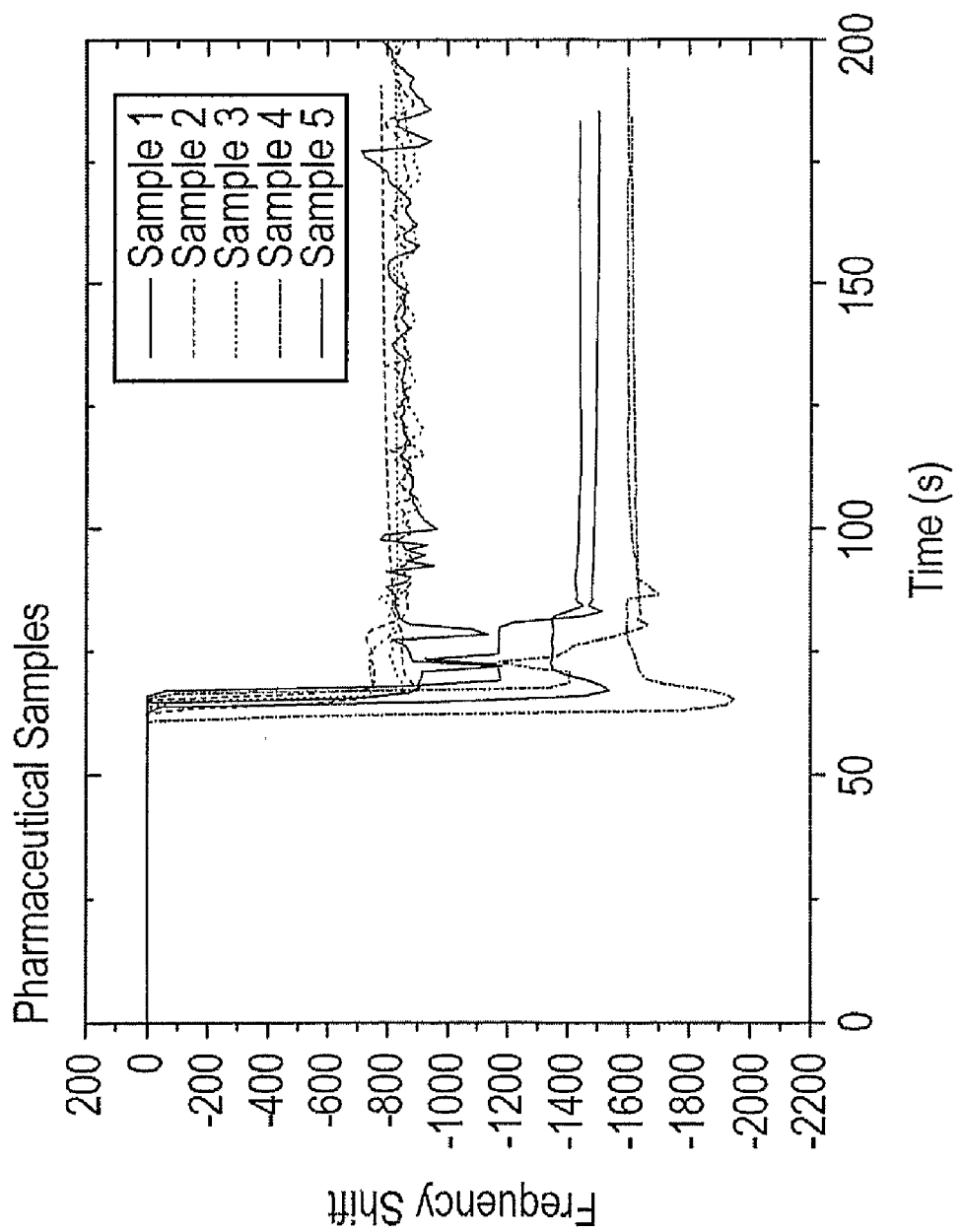
FIG. 12 shows a plot of frequency shift as a function of time as five different fluid samples were passed successively through a channel of apparatus according to an embodiment of the invention.

FIG. 12 shows a plot of frequency shift $\Delta F_r$ as a function of time for a series of fluids each containing a different one of five different pharmaceutical compounds. The fluids were passed through a flow cell according to an embodiment of the invention provided with a piezoelectric crystal.

A fluid was passed through the flow cell which was then cleaned and a different fluid passed through the flow cell. In each case, a sample of the same fluid was passed through the flow cell twice, the flow cell being cleaned between respective passes of the fluid.

The data from respective different samples are shown superimposed on one another to enable comparison. It can be seen that the data from each respective sample is highly reproducible. Thus, respective samples of the same fluid passed through the flow cell in different respective passes can be seen to have substantially the same value of frequency shift $\Delta F_r$.

In an alternative embodiment of the invention, a dip probe 200 (FIG. 13) is provided that is suitable for manual insertion into a fluid for the purpose of inspection of the fluid. The dip probe 200 is intended for use in analysing the content of fluids stored in environments where the fluid is immobile, such as tanks, ponds and storage containers.

Figure 13:
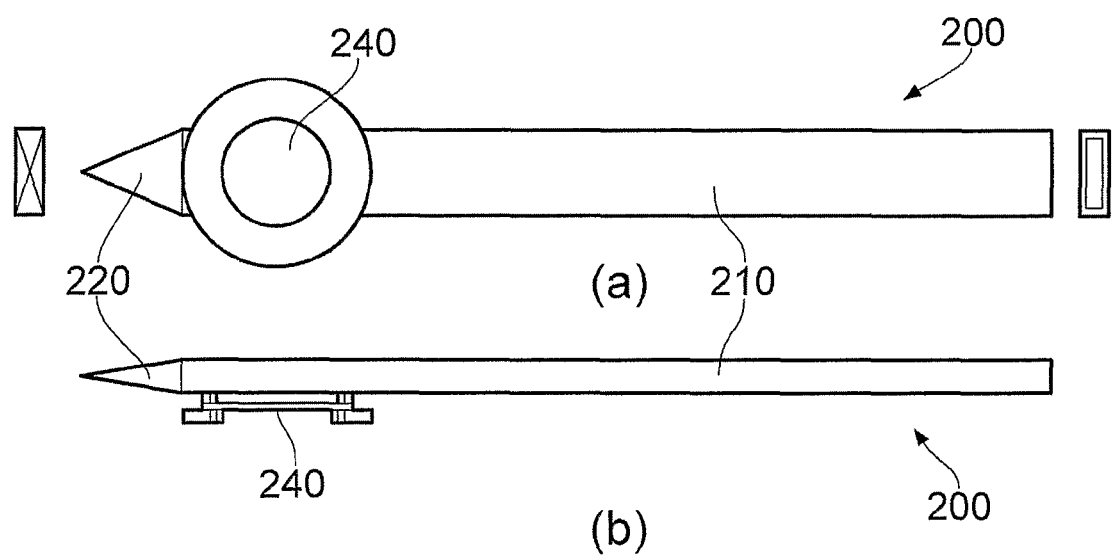
FIG. 13 shows a portable handheld probe according to an embodiment of the invention showing (a) a front elevation and (b) a cross-sectional view.

In the embodiment of FIG. 13, the probe 200 has a shaft 210 having a tapered end 220 configured for relatively easy insertion into a fluid, sludge or paste. A piezoelectric crystal 240 is provided on an outside of the shaft 210. The shaft 210 is shaped to have a relatively low cross-sectional area as viewed along a direction of flow of fluid past the probe 200 when the probe is in use. FIG. 13(b) shows a cross-section of the probe 200 along the intended direction of flow of fluid relative to the probe.

Figure 14:
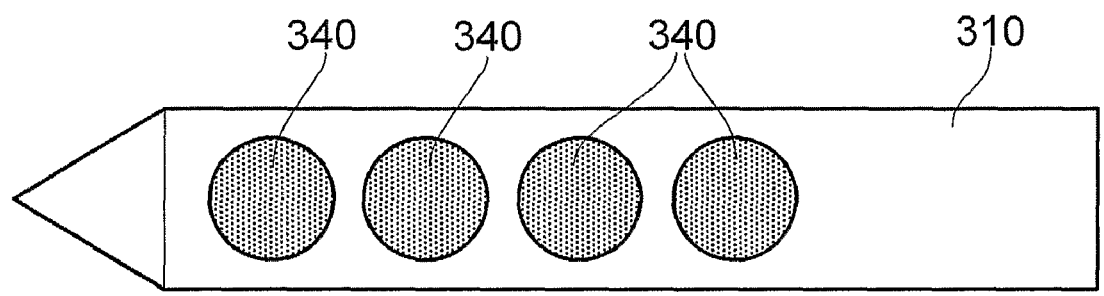
FIG. 14 is a front elevation of a further portable handheld probe according to an embodiment of the invention.

FIG. 14 shows a variation of the embodiment of FIG. 13 in which the probe has a shaft 310 provided with a plurality of piezoelectric crystals 340 along a length of the shaft. In some embodiments the crystals are provided with a protective cover that may be removed when required in order to allow individual crystals to be exposed. This feature has the advantage that the same probe may be used with a fresh crystal without a requirement to immediately replace the entire probe. For example, in the event that a crystal becomes damaged or otherwise unusable (e.g. due to chemical or mechanical attack) a fresh crystal may be made available without a requirement to replace the entire probe. In some embodiments the crystals are each provided with their own respective removable cover.

Figure 15A:
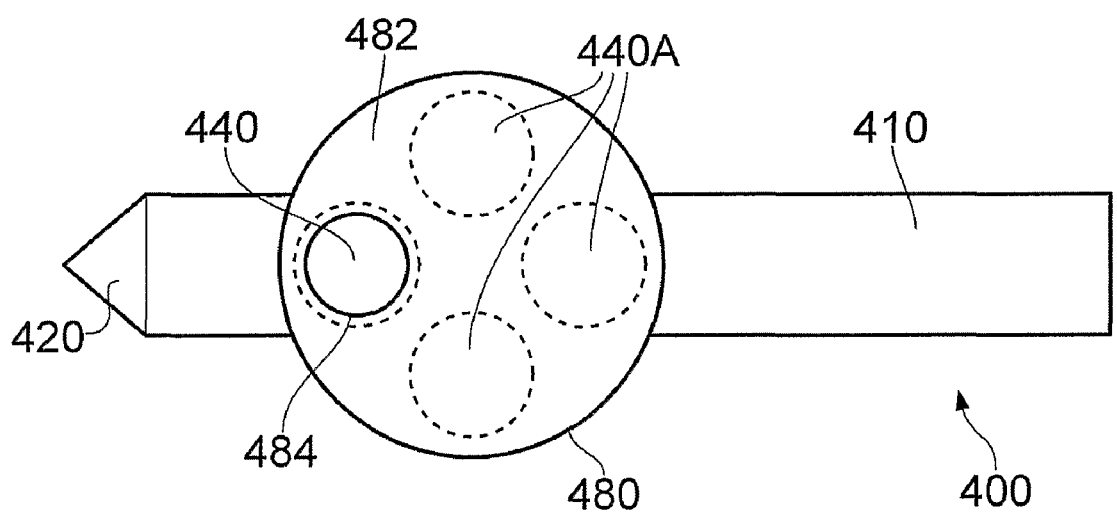
FIG. 15 shows (a) a front elevation of a further portable handheld probe, (b) a front elevation of a still further portable handheld probe and (c) a perspective view of a hand-held probe according to embodiments of the invention.
Figure 15B:
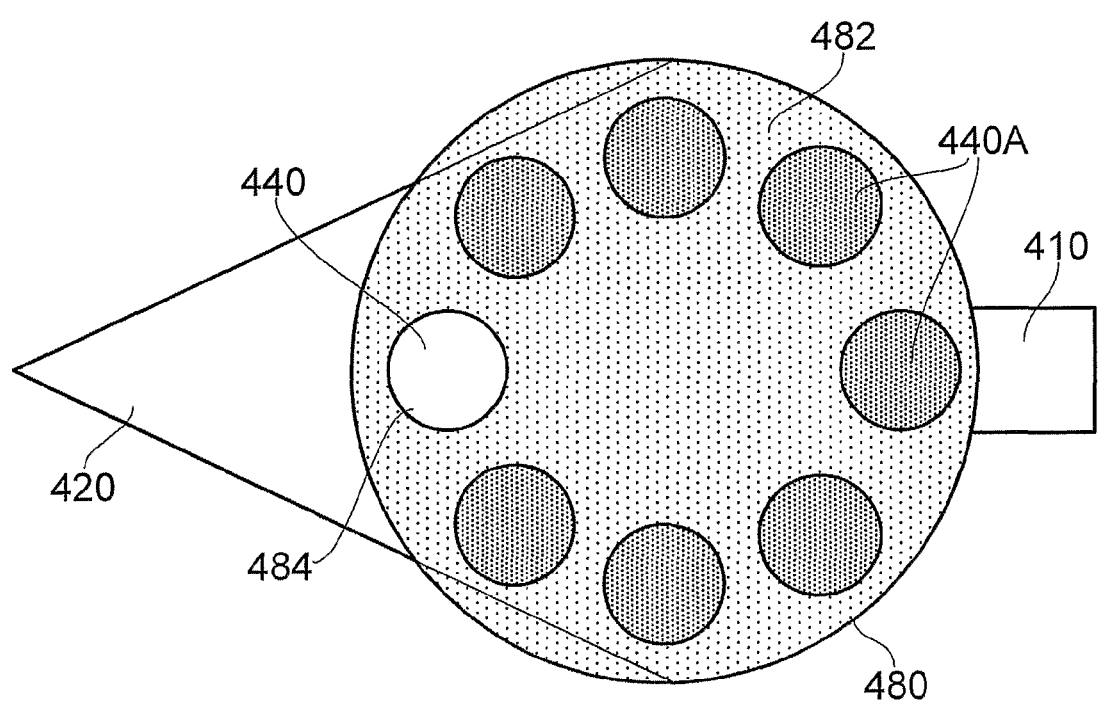

In some embodiments of the invention (e.g. the embodiments shown in FIG. 15(a), (b) where features common to both embodiments are labelled with the same reference numerals) probes 400 have a body portion 410 and are provided with a carousel 480 in which a plurality of piezoelectric crystals 440, 440A are provided. A rotatable cover portion 482 is provided that is arranged to enclose the crystals 440A in a watertight environment. The cover portion 482 has an aperture 484 arranged to expose one crystal 440 at a time to fluid. In the embodiment of FIG. 17(b) the probe is provided with a larger tapered end to provide additional strength and durability to the device.

When it is required to expose a fresh crystal to fluid, the cover portion 482 is rotated such that a further crystal 440A is exposed.

In some embodiments the carousel 480 is rotatable whilst the cover portion 482 is not rotatable.

The cover portion 482 may be formed from a transparent material such as glass, quartz or a transparent plastics material in order to allow a user visually to assess the state of crystals 440, 440A of the probe 400.

Other configurations of multiple crystals are also useful. In some embodiments a plurality of crystals may be exposed to a fluid at a given moment in time. In some such embodiments, depending on the intended application, crystals having similar or different resonant properties may be exposed simultaneously to a fluid and measurements made using the plurality of crystals to improve performance of the apparatus.

Figure 15C:
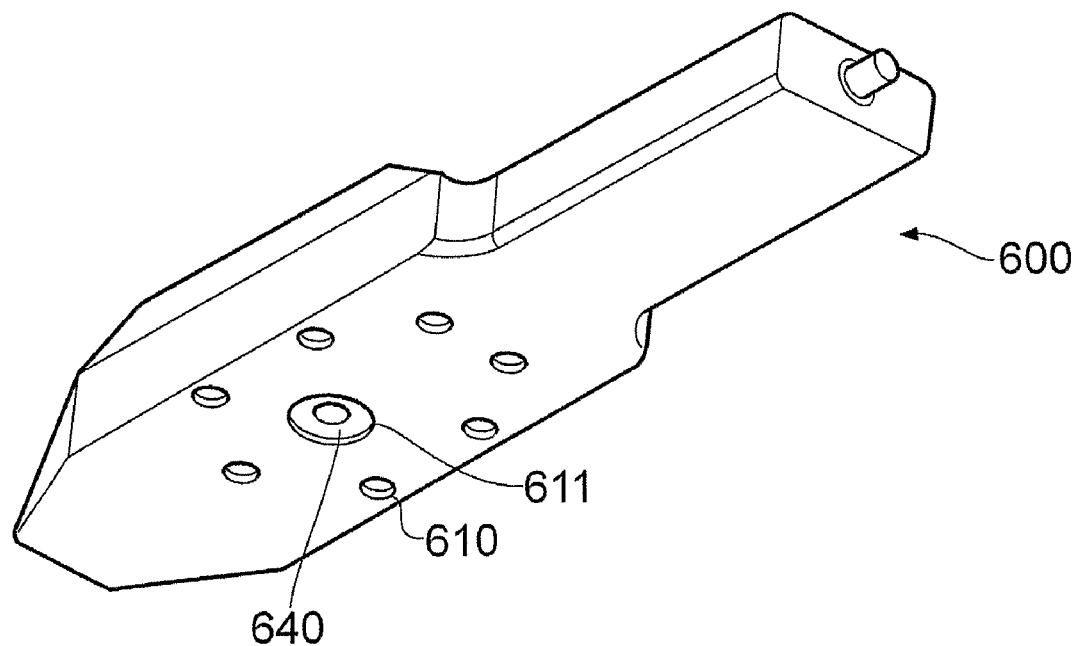

FIG. 15(c) shows a probe 600 according to an embodiment of the invention having a body portion 610 having an aperture 611 provided therein arranged to expose a piezoelectric crystal 440 to a fluid in which the probe 600 is dipped.

Apparatus according to some embodiments of the invention has an internal electrical circuit configured to provide an excitation potential to cause the piezoelectric crystal to oscillate at a resonant frequency of the crystal. The one or more crystals of the apparatus are provided with electrodes on opposed faces whereby a potential difference may be applied between the faces and oscillation of the one or more crystals induced by means of a known oscillator circuit.

Means are also provided for measuring a resonant frequency of oscillation of the crystal and means for determining a difference between the resonant frequency measured at a given moment in time and a reference resonant frequency being the resonant frequency of the crystal in air or other predetermined medium as discussed above.

Some embodiments of the invention are suitable for determining shear thinning/shear thickening behaviour of a fluid. In the case of a fluid exhibiting non-Newtonian behaviour, the viscosity of the fluid can be adjusted by shearing the fluid at different rates.

In some embodiments of the invention this is achieved by increasing the flow rate of fluid through a cell and measuring the viscosity as a function of flow rate.

An alternative way of achieving this is to increase or decrease the volumetric flow rate through a flow cell by introducing a constricting flow channel. As the flow area is reduced the flow velocity increases and the shear rate increases in a corresponding manner. A plurality of piezoelectric crystals can be provided along the channel to measure the measure viscosity at different respective positions which may be chose to correspond to different applied shear rates.

Figure 16:
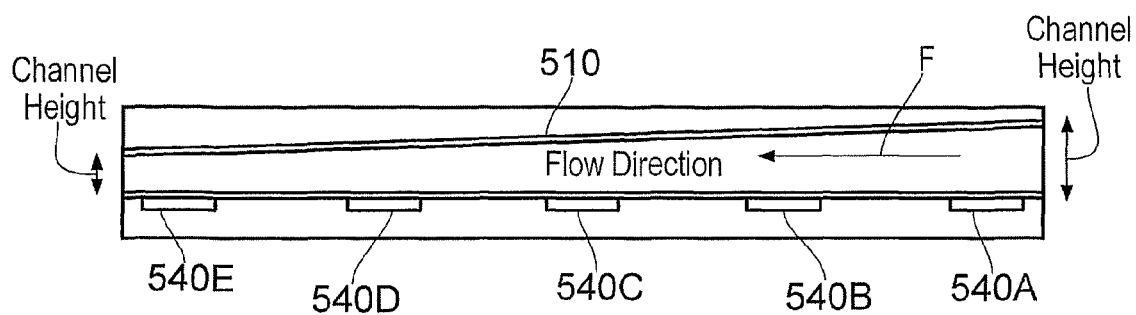
FIG. 16 is a schematic cross-sectional illustration of apparatus having a flow channel for determining shear thinning/shear thickening behaviour of a fluid.

An example of such a channel is shown in the embodiment of FIG. 16.

In the embodiment of FIG. 16 a flow channel 510 is provided having five piezoelectric crystals 540A to E provided in a wall of the flow channel 510. Other numbers of crystals are also useful.

The channel is arranged whereby a fluid flowing through the channel 510 in the direction of arrow F flows in contact with the five crystals 540A to E beginning with crystal 540A. By maintaining a generally constant volumetric flow rate through the channel 510 the flow velocity of the fluid will increase with distance along the channel 510.

Since the cross-sectional area of the channel 510 decreases along the direction of arrow F, respective crystals 540A to E are exposed to fluid that is experiencing increasing rates of shear. Other arrangements are also useful, for example the cross-sectional area of the channel may be arranged to increase along the direction of flow of fluid through the channel.

In some embodiments the change in cross-sectional area as a function of distance along the channel is linear. In some embodiments the change is non-linear.

Figure 17:
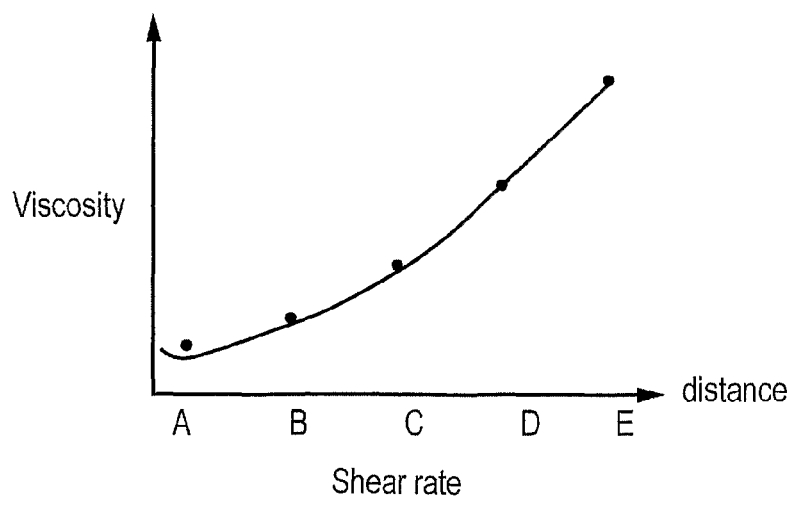
FIG. 17 is a plot of viscosity as a function of shear rate obtained using the apparatus of FIG. 16.

FIG. 17 shows a plot of viscosity (as determined by measuring a change in resonant frequency $\Delta F_r$ of the piezoelectric crystals relative to a reference frequency) as a function of shear rate (increased velocity), the data points corresponding to values of $\Delta F_r$ of different respective crystals 540 along the flow direction. It is to be understood that the x-axis of this plot (representing distance along the channel in the direction of fluid flow) can be calibrated to correspond to different respective values of shear rate, which increases with distance along the x-axis in the plot of FIG. 17.

Figure 18:
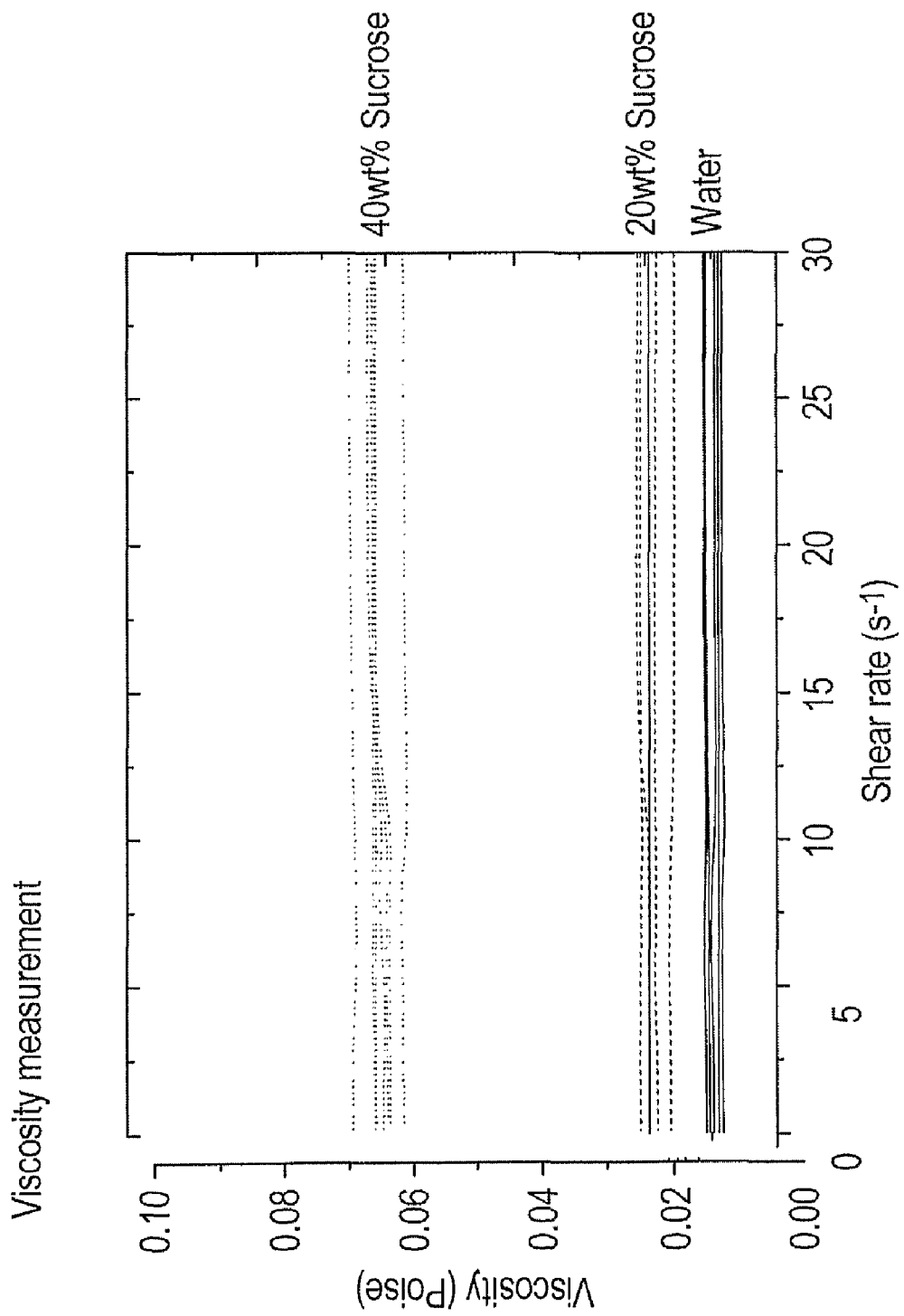
FIG. 18 is a plot of viscosity as a function of shear rate for a fluid having a sucrose content from 0 to around 40 weight percent obtained using the apparatus of FIG. 1

FIG. 18 shows a plot of viscosity (Poise) as a function of shear rate ($s^{-1}$) for water as a function of weight percent sucrose in the water. The data was obtained using apparatus according to the embodiment of FIG. 1(j), (k) by increasing a rate of flow of fluid through the channel of the apparatus as a function of time and measuring viscosity of the fluid in a substantially continuous manner as the rate of flow was increased.

The change in resonant frequency of the piezoelectric crystal was converted to a value of viscosity using a method disclosed in Kanazawa K K, Gordon J G, "The Oscillation Frequency of a quartz resonator in contact with a liquid", Analytica Chimica Acta, 1985, 175 pages 99 to 105 the content of which is hereby incorporated by reference.

The viscosity of water at 20° C. was taken to be 1.002 centiPoise

Figure 19A:
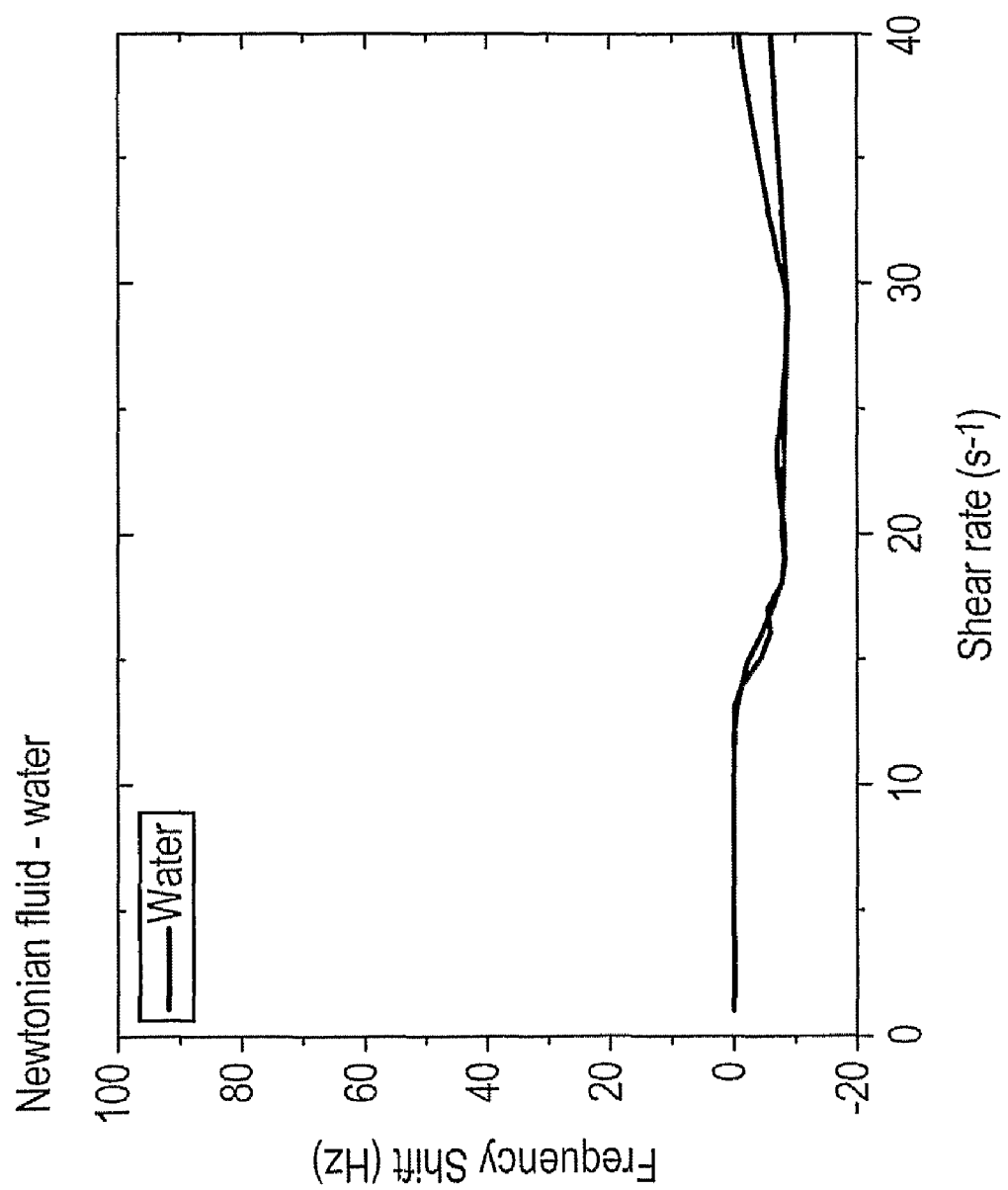
FIG. 19 is a plot of resonant frequency shift of a piezoelectric crystal relative to a reference frequency as a function of shear rate when the crystal is exposed to (a) water (Newtonian fluid); (b) a first pharmaceutical composition (non-Newtonian fluid) and (c) a second pharmaceutical composition (non-Newtonian fluid)

FIG. 19(a) shows a plot of frequency shift $\Delta F_r$ as a function of shear rate for a Newtonian fluid (water). It can be seen that the change in resonant frequency $\Delta F_r$ of the piezoelectric device is negligible as shear rate increases.

Figure 19B:
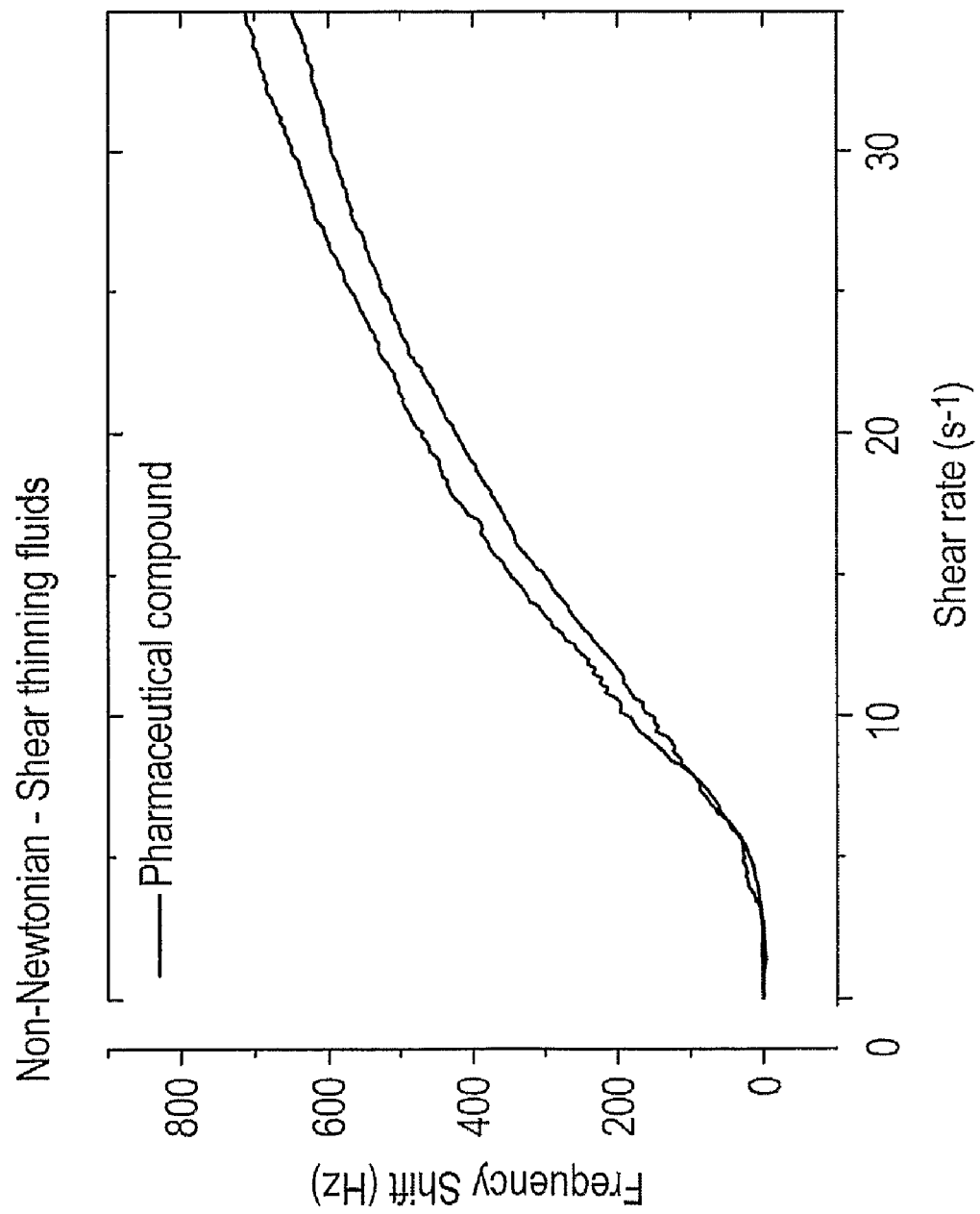

FIG. 19(b) shows a plot of frequency shift $\Delta F_r$ as a function of shear rate for a non-Newtonian fluid. The fluid is water containing a pharmaceutical compound, the fluid being a fluid that exhibits shear-thinning. In other words, as the fluid is subject to a shear stress a viscosity of the fluid decreases. The frequency shift $\Delta F_r$ changes accordingly and it can be seen that $\Delta F_r$ increases as a function of shear rate. Data obtained for samples of fluid of the same nominal compositions at different respective times are shown in the figure. Similarity of the plots indicates that the measurements are highly reproducible.

FIG. 19(c) shows a plot of frequency shift $\Delta F_r$ as a function of shear rate for a further pharmaceutical compound in water. It can be seen that the frequency shift $\Delta F_r$ increases as a function of shear rate. As in the case of FIG. 19(b) data obtained for samples of fluid of the same nominal composition at different respective times are shown in the figure. Similarity of the plots corresponding to a fluid of a given composition indicate that the measurements are highly reproducible.

Embodiments of the invention such as that of FIG. 16 have the advantage that a full flow curve analysis of a fluid can be obtained in a matter of a few seconds or less. In other words, in some embodiments values of viscosity at different values of shear rate can be obtained in a matter of a few seconds of less. Some embodiments of the invention allow values of viscosity to be obtained at different values of shear rate substantially simultaneously.

This is in contrast to prior art methods of measuring shear rate requiring a plurality of steady state flow rates of a fluid in a chamber of constant cross-sectional area to be attained for successive periods of time. According to such methods, measurements of viscosity of the fluid are made using conventional means when steady state flow conditions are achieved, at each respective different flow rate.

Apparatus according to some embodiments of the invention can also be used to measure surface charge.

It is known that the rheological properties of a fine particulate sludge, fluid or complex fluid can be manipulated through control of the surface charge. Thus, measurement of the surface charge can assist in characterising the rheological properties of a fluid. For example, such data can be helpful in predicting flow behaviour, sedimentation behaviour, consolidation etc.

In some industrial processes, surface charge is controlled through manipulation of solution chemistry (in particular, ionic concentration and pH).

Traditionally, the surface charge on a colloid particle is determined through electrophoresis whereby charged particles in a solution are attracted to an electrode of opposite charge. The migration rate of particles to the electrode is dependent upon the charge density and may be used to calculate the particle surface charge.

The present inventors have found that if the amplitude of oscillation of a piezoelectric crystal in contact with a fluid is increased, a shift in resonant frequency of the crystal may be observed. The shift in resonant frequency is related to particle-particle contact mechanics which are a function of particle surface charge.

A step increase in amplitude of oscillation is found to causes a step change in resonant frequency of the piezoelectric crystal. The magnitude of the change in resonant frequency diminishes as amplitude of oscillation increases until, above a 'saturation amplitude', no significant change in resonant frequency is observed as the amplitude of oscillation is further increased. The present inventors have found that the change in resonant frequency at the saturation amplitude relative to a constant reference resonant frequency is proportional to the amount of surface charge on particles of the fluid.

In some embodiments of the invention oscillation of the piezoelectric crystal generates a transverse acoustic wave with a relatively low longitudinal wave effect.

In some embodiments of the present invention, the frequency response of a resonating crystal in contact with a suspension of particles is measured as the amplitude of oscillation of the crystal is increased. Amplitude 'sweeping' may be employed whereby the amplitude of oscillation of the crystal is increased as a function of time. In some embodiments a series of step increases in amplitude are generated as a function of time. In some embodiments a relatively smooth or continuous increase in amplitude is generated.

Figure 20:
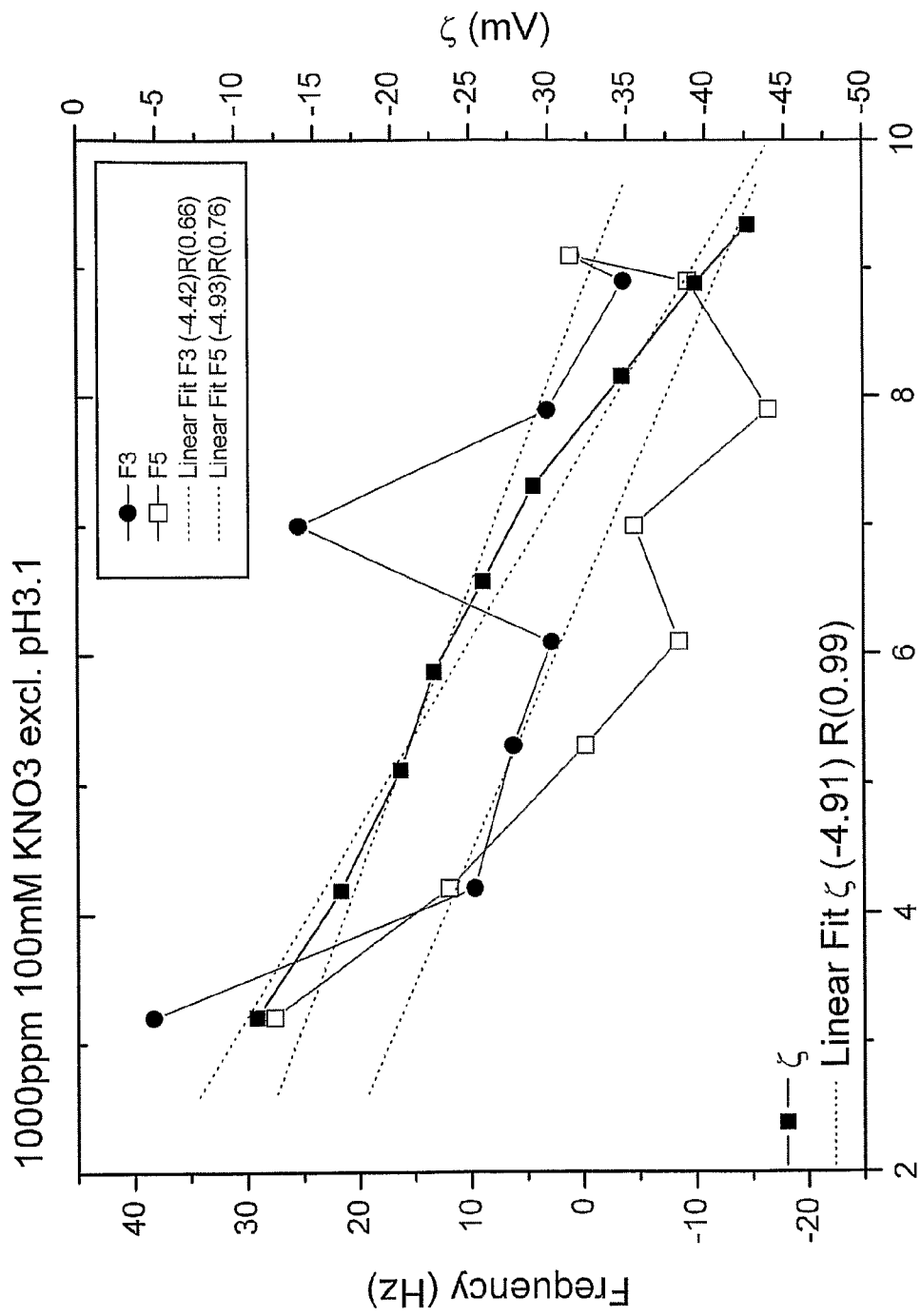
FIG. 20 is a plot showing resonant frequency (left hand vertical axis) of a piezoelectric crystal as a function of suspension pH (horizontal axis) obtained using apparatus according to an embodiment of the invention together with corresponding values of zeta potential (surface charge) of the suspension (right hand vertical axis) as measured using prior art zeta potential measurement apparatus.

FIG. 20 shows a plot of frequency shift (Hz) of the resonant frequency relative to a reference frequency as a function of pH for a fluid comprising silica spheres around 1 μm in diameter in a 0.1M aqueous $KNO_3$ solution.

Data points in the Figure obtained from the apparatus are in respect of changes in resonant frequencies at the F3 and F5 positions of the crystal. It is to be understood that changes in resonant frequency at other positions of the crystal, such as F1 (the resonant frequency at a generally central position of the crystal) and other positions are also useful.

It can be seen that the resonant frequency of the crystal decreases as pH increases. By way of comparison, measurements of the zeta potential $\zeta$ of the fluid using a separate technique are plotted in the same Figure. It can be seen that the rate of change of zeta potential $\zeta$ as a function of pH is comparable to the rate of change of frequency shift of the piezoelectric crystal.

The phenomenon is understood to be due at least in part to changes in surface charge of particles of the fluid due to changes in contact or bridging mechanics between the particles. Such changes result in structural changes to the fluid.

Embodiments of the invention configured to measure frequency change as amplitude of oscillation is increased are also useful in measuring properties of polymeric and biological fluids.

In some embodiments of the invention apparatus is provided that is configured to convert measurements of changes in a resonant frequency of a piezoelectric crystal to corresponding changes in a value of a zeta potential $\zeta$ of the fluid.

Thus in some embodiments a change in resonant frequency of the apparatus as a function of pH may be converted to a corresponding change in zeta potential $\zeta$ following calibration of the apparatus with measurements made by a separate zeta potential measurement technique.

It will be appreciated that embodiments of the invention are suitable for use in a wide range of applications including the food industry, agricultural industry, water treatment industry and the nuclear industry where analysis of fluids including pastes and slurries is required. Embodiments of the invention provide a reliable means for characterising one or more properties of such fluids.

For example in some embodiments of the invention nuclear slurries and other sludges and sludge-like materials are arranged to be brought into contact with a piezoelectric element and one or more properties of the material investigated. For example, yield stress of the material, solids concentration and/or viscosity may be measured.

Correlation of one or more of these characteristics with other characteristics of the material may then be made.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. Apparatus for inspection of a fluid comprising:
  a channel portion, the channel portion having a channel inlet and a channel outlet separate from the channel inlet;
  a piezoelectric sensor element provided at a sensor position of the channel and arranged to contact fluid flowing through the channel portion from said channel inlet to said channel outlet,
  the apparatus being configured to determine a difference value $\Delta F_r$ being a value corresponding to a difference between a resonant frequency of oscillation of said piezoelectric element at a given moment in time and a reference resonant frequency.

2. Apparatus as claimed in claim 1 wherein the piezoelectric sensor element is provided at a wall of the channel.

3. Apparatus as claimed in claim 1 wherein a plane of a face of the sensor element exposed to fluid flowing through said channel is oriented generally parallel to a direction of flow of fluid through said channel.

4. Apparatus as claimed in claim 1 wherein the channel is shaped to promote fully developed laminar flow of fluid through the channel at the sensor position.

5. Apparatus as claimed in claim 1 wherein the channel is provided with a build-up portion, the build-up portion comprising a length of the channel spanning a distance from the piezoelectric element in a direction towards the inlet, the build-up portion being of substantially constant cross-sectional area.

6. Apparatus as claimed in claim 1 wherein the channel portion is shaped and configured whereby a fluid flowing through the channel portion experiences squeeze flow whereby the channel is substantially entirely filled with fluid.

7. Apparatus as claimed in claim 1 wherein the apparatus is provided with a swirl pipe generally upstream of the channel, the swirl pipe being configured to develop swirl in a fluid flowing into the channel.

8. Apparatus as claimed in claim 1 wherein the channel outlet is provided with a bend portion whereby the direction of fluid flow from said channel is changed.

9. Apparatus as claimed in claim 1 comprising a plurality of piezoelectric elements at mutually spaced apart locations along a length of the channel, the elements being arrange to contact fluid flowing through the channel.

10. Apparatus as claimed in claim 1 wherein the inlet has an inlet aperture of a first diameter and the outlet has an outlet aperture of a second diameter wherein the first and second diameters are in the range from around 1 μm to around 100 mm.

11. Apparatus as claimed in claim 1 wherein the reference resonant frequency corresponds to that of a further piezoelectric crystal arranged to be isolated from the fluid flowing through the channel portion whereby the fluid does not contact the further piezoelectric crystal.

12. Apparatus as claimed in claim 1 further arranged to measure an amount of surface charge of particles comprised in the fluid,
the apparatus being configured to cause the piezoelectric element to oscillate at a resonant frequency of the element at a first amplitude of oscillation, the apparatus being further arranged to increase an amplitude of oscillation of the element above the first amplitude until a final amplitude of oscillation is attained whereat a rate of change of resonant frequency with amplitude of oscillation is below a prescribed rate,
the apparatus being further configured to provide an output corresponding to an amount of surface charge of particles of the fluid based on a difference between the final resonant frequency data value and a reference resonant frequency value, the reference resonant frequency value corresponding to a reference resonant frequency, the reference resonant frequency being the resonant frequency of the element under predetermined conditions, which predetermined conditions optionally correspond to room temperature and standard pressure.

13. Apparatus as claimed in claim 1 arranged to provide an output corresponding to a value of either: a yield stress of the fluid based on the difference value $\Delta F_r$; a solids concentration of the fluid based on the difference value $\Delta F_r$; or a viscosity of the fluid based on the difference value $\Delta F_r$.

14. A dip probe device for inspection of a fluid comprising:
a body portion; and
a piezoelectric element coupled to the body portion,
the device being operable to expose the piezoelectric element to a fluid in which the device is dipped, the device being further operable to excite said element thereby to induce oscillation of the element at a resonant frequency of the element, the apparatus being configured to determine a difference value corresponding to a value of a difference between the resonant frequency of said piezoelectric element at a given moment in time and a reference frequency being the resonant frequency of the element under predetermined conditions, which predetermined conditions optionally correspond to room temperature and standard pressure.

15. A device as claimed in claim 14 wherein the body portion is provided with a free end having a tapered form.

16. A device as claimed in claim 14 wherein a thickness of the body portion is lower along a direction perpendicular to a plane of the piezoelectric element compared with that along a direction parallel the plane of the piezoelectric element.

17. A device as claimed in claim 14 comprising a plurality of piezoelectric elements.

18. A method of inspecting a fluid comprising the steps of:
passing a fluid through a channel having a channel inlet and channel outlet, the channel being provided with a piezoelectric sensor element at a sensor position of the channel, the element being arranged to contact fluid flowing through the channel portion from said channel inlet to said channel outlet;
determining a difference value $\Delta F_r$ being a value corresponding to a difference between a resonant frequency of oscillation of said piezoelectric element at a given moment in time and a reference resonant frequency.

19. A method as claimed in claim 18 further comprising the step of providing an output corresponding to the value of the yield stress of the fluid based on the difference value $\Delta F_r$.

20. A method as claimed in claim 18 further comprising the step of performing a calibration operation.

21. A method as claimed in claim 18 further comprising measuring an amount of surface charge of particles of a fluid.

22. A method as claimed in claim 21 comprising the steps of:
(a) placing the piezoelectric element in contact with the fluid to be measured;
(b) causing the element to oscillate at a resonant frequency of the element;
(c) increasing the amplitude of oscillation of the element until a rate of change of resonant frequency with amplitude is less than a predetermined threshold value, the value of the amplitude of oscillation at this stage being a final amplitude value;
(d) obtaining a data value corresponding to a final resonant frequency of the element being the resonant frequency when the element is in contact with the fluid and the element is oscillating at the final amplitude value;
(e) providing an output corresponding to an amount of surface charge of particles of the fluid based on a difference between the data value and a reference value corresponding to a reference resonant frequency, the reference resonant frequency being the resonant frequency of the element under predetermined conditions, which predetermined conditions optionally correspond to room temperature and standard pressure.

23. A method as claimed in claim 22 wherein the apparatus is configured to provide said output in the form of a value of a zeta potential of the fluid.

24. A method as claimed in claim 18 further comprising at least one of: the step of determining a viscosity of the fluid based on the resonant frequency difference value $\Delta F_r$; and the step of determining a solids concentration of the fluid based on the resonant frequency difference value $\Delta F_r$.

* * * * *